United States Patent
Ostroff

(10) Patent No.: US 9,682,135 B2
(45) Date of Patent: *Jun. 20, 2017

(54) DRUG DELIVERY PRODUCT AND METHODS

(71) Applicant: UNIVERSITY OF MASSACHUSETTS, Boston, MA (US)

(72) Inventor: Gary R. Ostroff, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 100 days.

This patent is subject to a terminal disclaimer.

(21) Appl. No.: 14/073,216

(22) Filed: Nov. 6, 2013

(65) Prior Publication Data

US 2014/0335047 A1    Nov. 13, 2014

Related U.S. Application Data

(63) Continuation of application No. 12/781,549, filed on May 17, 2010, now Pat. No. 8,580,275, which is a continuation of application No. 10/869,693, filed on Jun. 16, 2004, now Pat. No. 7,740,861.

(51) Int. Cl.

| | |
|---|---|
| *A61K 36/06* | (2006.01) |
| *A61K 39/125* | (2006.01) |
| *A61K 9/50* | (2006.01) |
| *A61K 48/00* | (2006.01) |
| *A61K 31/65* | (2006.01) |
| *C12N 7/00* | (2006.01) |
| *C12N 15/113* | (2010.01) |
| *A61K 39/00* | (2006.01) |

(52) U.S. Cl.
CPC .......... *A61K 39/125* (2013.01); *A61K 9/5068* (2013.01); *A61K 9/5073* (2013.01); *A61K 31/65* (2013.01); *A61K 48/0008* (2013.01); *A61K 48/0025* (2013.01); *A61K 48/0041* (2013.01); *C12N 7/00* (2013.01); *C12N 15/113* (2013.01); *A61K 2039/53* (2013.01); *A61K 2039/6087* (2013.01); *C12N 2770/32234* (2013.01)

(58) Field of Classification Search
None
See application file for complete search history.

(56) References Cited

U.S. PATENT DOCUMENTS

| | | | |
|---|---|---|---|
| 3,737,337 A | 6/1973 | Pampus et al. | |
| 3,891,570 A | 6/1975 | Fukushima et al. | |
| 4,160,452 A | 7/1979 | Theeuwes | |
| 4,256,108 A | 3/1981 | Theeuwes | |
| 4,265,874 A | 5/1981 | Bonsen et al. | |
| 4,384,975 A | 5/1983 | Fong | |
| 4,389,330 A | 6/1983 | Tice et al. | |
| 4,595,660 A | 6/1986 | Ostroff et al. | |
| 4,652,441 A | 3/1987 | Okada et al. | |
| 4,663,308 A | 5/1987 | Saffran et al. | |
| 4,777,049 A | 10/1988 | Magruder et al. | |
| 4,810,646 A | 3/1989 | Jamas et al. | |
| 4,946,778 A | 8/1990 | Ladner et al. | |
| 4,956,778 A | 9/1990 | Naito | |
| 4,992,540 A | 2/1991 | Jamas et al. | |
| 5,028,703 A | 7/1991 | Jamas et al. | |
| 5,032,401 A | 7/1991 | Jamas et al. | |
| 5,082,936 A | 1/1992 | Jamas et al. | |
| 5,091,513 A | 2/1992 | Huston et al. | |
| 5,132,405 A | 7/1992 | Huston et al. | |
| 5,322,841 A | 6/1994 | Jamas et al. | |
| 5,401,727 A | 3/1995 | Rorstad et al. | |
| 5,407,609 A | 4/1995 | Tice et al. | |
| 5,488,040 A | 1/1996 | Jamas et al. | |
| 5,504,079 A | 4/1996 | Jamas et al. | |
| 5,532,223 A | 7/1996 | Jamas et al. | |
| 5,545,806 A | 8/1996 | Lonberg et al. | |
| 5,569,825 A | 10/1996 | Lonberg et al. | |
| 5,607,677 A | 3/1997 | Jamas et al. | |
| 5,622,939 A | 4/1997 | Jamas et al. | |
| 5,622,940 A | 4/1997 | Ostroff | |
| 5,663,324 A | 9/1997 | James et al. | |
| 5,663,369 A | 9/1997 | Kreutzer et al. | |
| 5,705,153 A | 1/1998 | Shorr et al. | |

(Continued)

FOREIGN PATENT DOCUMENTS

| | | |
|---|---|---|
| EP | 0242135 A2 | 10/1987 |
| JP | 4-117245 | 4/1992 |

(Continued)

OTHER PUBLICATIONS

Erbacher, Patrick et al., "The reduction of the positive charges of polylysine by partial gluconoylation increases the transfection efficiency of polylysine/DNA complexes," Biochimica et Biophysica Acta, vol. 1324:27-36 (1997).

Erickson, Ann H. et al., "Biosynthesis of the Lysosomal Enzyme Glucocerebrosidase," The Journal of Biological Chemistry, vol. 260:14319-14324 (1985).

Eto. Y. et al., "Treatment of lysosomal storage disorders: Cell therapy and gene therapy," J. Inherit Metab. Dis., vol. 27:411-415 (2004).

Fabrega, Sylvie et al., "Human glucocerebrosidase: heterlogous expression of active site mutants in murine null cells," Glycobiology, vol. 10(11):1217-1224 (2000).

(Continued)

*Primary Examiner* — Chris R Tate
*Assistant Examiner* — Randall Winston
(74) *Attorney, Agent, or Firm* — Lathrop & Gage LLP; James H. Velema, Esq.

(57) ABSTRACT

The present invention provides a particulate delivery system comprising an extracted yeast cell wall comprising beta-glucan, a payload molecule and a payload trapping molecule. The invention further provides methods of making and methods of using the particulate delivery system.

15 Claims, 8 Drawing Sheets

(56) References Cited

U.S. PATENT DOCUMENTS

| | | | |
|---|---|---|---|
| 5,741,495 A * | 4/1998 | Jamas | A61K 9/1652 424/278.1 |
| 5,783,569 A | 7/1998 | Jamas et al. | |
| 5,811,542 A | 9/1998 | Jamas et al. | |
| 5,814,318 A | 9/1998 | Lonberg et al. | |
| 5,817,643 A | 10/1998 | Jamas et al. | |
| 5,849,720 A | 12/1998 | Jamas et al. | |
| 5,879,680 A | 3/1999 | Ginns et al. | |
| 5,911,983 A | 6/1999 | Barranger et al. | |
| 5,968,811 A | 10/1999 | Greenshields | |
| 6,022,703 A | 2/2000 | Long et al. | |
| 6,074,864 A | 6/2000 | Ginns et al. | |
| 6,118,045 A | 9/2000 | Reuser et al. | |
| 6,133,229 A | 10/2000 | Gibson et al. | |
| 6,214,586 B1 * | 4/2001 | McNeilly | C12N 15/101 435/252.8 |
| 6,369,216 B1 | 4/2002 | Patchen et al. | |
| 6,372,499 B1 | 4/2002 | Midoux et al. | |
| 6,379,965 B1 | 4/2002 | Boutin | |
| 6,420,176 B1 * | 7/2002 | Lisziewicz | A61K 31/17 435/455 |
| 6,444,448 B1 | 9/2002 | Wheatcroft et al. | |
| 6,476,003 B1 | 11/2002 | Jordan et al. | |
| 6,495,570 B2 | 12/2002 | Jacob et al. | |
| 6,512,097 B1 | 1/2003 | Marks et al. | |
| 6,696,272 B1 | 2/2004 | Mahuran et al. | |
| 6,740,336 B2 | 5/2004 | Trubetskoy et al. | |
| 6,846,809 B2 | 1/2005 | Cristiano et al. | |
| 6,855,808 B2 | 2/2005 | Goto et al. | |
| 7,018,986 B2 | 3/2006 | Sorgente et al. | |
| 7,022,685 B2 | 4/2006 | Patchen et al. | |
| 7,220,427 B2 | 5/2007 | Jordan | |
| 7,229,623 B1 * | 6/2007 | Cheever | C07K 14/71 424/185.1 |
| 7,740,861 B2 * | 6/2010 | Ostroff | A61K 9/5068 424/195.16 |
| 8,007,814 B2 * | 8/2011 | Ginns | A61K 9/5068 424/195.16 |
| 8,580,275 B2 * | 11/2013 | Ostroff | A61K 9/5068 424/195.16 |
| 8,637,045 B2 | 1/2014 | Ginns | |
| 2002/0032170 A1 | 3/2002 | Jamas et al. | |
| 2002/0143174 A1 | 10/2002 | Patchen et al. | |
| 2003/0207827 A1 | 11/2003 | Boyle et al. | |
| 2003/0216346 A1 | 11/2003 | Sakurai et al. | |
| 2004/0014715 A1 | 1/2004 | Ostroff | |
| 2004/0116380 A1 | 6/2004 | Jamas et al. | |
| 2004/0162235 A1 | 8/2004 | Trubetskoy et al. | |
| 2005/0245480 A1 | 11/2005 | Ostroff et al. | |
| 2005/0255487 A1 | 11/2005 | Khvorova et al. | |
| 2005/0281781 A1 | 12/2005 | Ostroff | |
| 2006/0083718 A1 | 4/2006 | Ginns et al. | |
| 2006/0134663 A1 | 6/2006 | Harkin et al. | |
| 2006/0160133 A1 | 7/2006 | Czech et al. | |
| 2006/0165700 A1 | 7/2006 | Ostroff et al. | |
| 2006/0247205 A1 | 11/2006 | Patchen et al. | |
| 2007/0213284 A1 | 9/2007 | Sohail et al. | |
| 2008/0044438 A1 | 2/2008 | Ostroff et al. | |
| 2008/0220038 A1 | 9/2008 | Franklin et al. | |
| 2009/0209624 A1 | 8/2009 | Ginns | |
| 2012/0070376 A1 | 3/2012 | Ostroff et al. | |

FOREIGN PATENT DOCUMENTS

| | | |
|---|---|---|
| JP | 9-67205 | 3/1997 |
| JP | 2006-502167 | 1/2006 |
| JP | 2007-516687 | 6/2007 |
| JP | 2007-531700 | 11/2007 |
| JP | 2008-503472 | 2/2008 |
| WO | 89/05850 A1 | 6/1989 |
| WO | 90/15596 A1 | 6/1990 |
| WO | 91/03248 A2 | 3/1991 |
| WO | 91/03495 A1 | 3/1991 |
| WO | 92/07064 A1 | 4/1992 |
| WO | 94/04163 A1 | 3/1994 |
| WO | 00/18411 A1 | 4/2000 |
| WO | 02/12348 A2 | 2/2002 |
| WO | 03/041509 A1 | 5/2003 |
| WO | 2004/012657 A2 | 2/2004 |
| WO | 2004/014320 A2 | 2/2004 |
| WO | 2004/021994 A2 | 3/2004 |
| WO | 2004/037232 A1 | 5/2004 |
| WO | 2004/053103 A1 | 6/2004 |
| WO | 2004/053103 A2 | 6/2004 |
| WO | 2005/014776 A2 | 2/2005 |
| WO | 2005/018544 A2 | 3/2005 |
| WO | PCT/US05/21161 | 6/2005 |
| WO | WO 2006/007372 | 6/2005 |
| WO | 2006/007372 A2 | 1/2006 |
| WO | 2006/032039 A2 | 3/2006 |
| WO | 2007/050643 A2 | 5/2007 |
| WO | 2007/099387 A1 | 9/2007 |
| WO | 2007/109564 A2 | 9/2007 |
| WO | 2009/058913 A2 | 5/2009 |

OTHER PUBLICATIONS

Fattal, Elias et al., "State of the art and perspectives for the delivery of antisense oligonucleotides and siRNA polymeric nanocarriers," International Journal of Pharmaceutics, vol. 364:237-248 (2008).

Felgner, Philip L. et al., "Lipofection: A highly efficient, lipid-mediated DNA-transfection procedure," Proc. Natl. Acad. Sci. USA, vol. 84:7413-7417 (1987).

Filleur, Stephanie et al., "SiRNA-mediated Inhibition of Vascular Endothelial Growth Factor Severely Limits Tumor Resistance to Antiangiogenic Thrombospondin-1 and Slows Tumor Vascularization and Growth," Cancer Research, vol. 63:3919-3922 (2003).

Fromen-Romano, Cecile et al., "Transformation of a non-enzymatic toxin into a toxoid by genetic engineering," Protein Engineering, vol. 10(10):1213-1220 (1997).

GenBank Accession No. 126:207866, Erbacher, Patrick et al., "The reduction of the positive charges of polylysine by partial gluconoylation increases the transfection efficiency of polylysine/DNA complexes," Biochim. Biophys. Acta, vol. 1324(1):27-36 (1997).

Germain, Dominiuqe P., "Fabry disease: recent advances in enzyme replacement therapy," Expert Opin. Investig. Drugs, vol. 11(10):1467-1476 (2002).

Grabowski, Gregory A.,"Gaucher Disease: Lessons from a Decade of Therapy," J. Pediatr., vol. 144:S15-S19 (2004).

Guilherme, Adilson et al., "Adipocyte dysfunctions linking obesity to insulin resistance and type 2 diabetes," Nature Reviews, Molecular Cell Biology, vol. 9:367-377 (2008).

Hiraiwa, Masao et al., "Isolation, Characterization, and Proteolysis of Human Prosaposin, the Precursor of Saposins (Sphingolipid Activator Proteins)," Archives of Biochemistry and Biophysics, vol. 304(1):110-116 (1993).

Hong, Feng et al., "Beta-Glucan Functions as an Adjuvant for Monoclonal Antibody Immunotherapy by Recruiting Tumoricidal Granulocytes as Killer Cells," Cancer Research, vol. 63:9023-9031 (2003).

Hong, Feng et al., "Mechanism by Which Orally Administered Beta-1,3-Giucans Enhance the Tumoricidal Activity of Antitumor Monoclonal Antibodies in Murine Tumor Models," The Journal of Immunology, vol. 173:797-806 (2004).

Howell, Mark D. et al., "Limited T-cell receptor b-chain heterogeneity among interleukin 2 receptor-positive synovial T cells suggests a role for superantigen in rheumatoid arthritis," Proc. Natl. Acad. Sci. USA, vol. 88:10921-10925 (1991).

Huang, Haibin et al., "Distinct Patterns of Dendritic Cell Cytokine Release Stimulated by Fungal Beta-Glucans and Toll-Like Receptor Agonists," Infection and Immunity, vol. 77(5):1774-1781 (2009).

Huang, Haibin et al., "Robust Stimulation of Humoral and Cellular Immune Responses following Vaccination with Antigen-Loaded Beta-Giucan Particles," mBio, vol. 1(3):e00164-10, 7 pages, (2010).

(56) References Cited

OTHER PUBLICATIONS

Ishii, Tsuyoshi et al., "Mechanism of cell transfection with plasmid/chitosan complexes," Biochimica eta Biophysica Acta, vol. 1514:51-64 (2001).
Jamas, S. et al., "PGG-Giucans, A Novel Class of Macrophage-Activating Immunomodulators," Polymeric Drugs and Drug Delivery Systems, ACS Symposium Series, Chapter 5:44-51 (1991).
Jamas, S. et al., "PGG—A Novel Class of Macrophage Activating Immunomodulators," Polymer Preprints, vol. 31 (2):194-195 (1990).
JAVMA News, "Rheumatoid arthritis has no cure, but treatmens exhist," retrieved online at http://www.avma/org/onlnews/javma/may09/090515u_pf.asp, 2 pages (2009).
Jepson, Mark A. et al., "M cell targeting by lectins: a strategy for mucosal vaccination and drug delivery," Advanced Drug Delivery Reviews, vol. 56:511-525 (2004).
Khoury, Maroun et al., "Efficient New Cationic Liposome Formulation for Systemic Delivery of Small Interfering RNA Silencing Tumor Necrosis Factor alpha in Experimental Arthritis," Arthritis & Rheumatism, vol. 54(6):1867-1877 (2006).
Lee et al. 'Specific Treatment for Lysosomal Storage Disorders: Enzyme Replacement Therapy, Bone Marrow Transplant and Others'. HK J Paediatric. 2004, vol. 9, pp. 231-239.
Fan "A contradictory treatment for lysosomal storage disorders: inhibitors enhance mutant enzyme activity." Trends in pharmacological sciences 24.7 (2003): 355-360.
Canadian Office Action for Application No. 2,580,537 dated Apr. 25, 2013 (2 pages).
Kim, Tae Hee et al., "Synergistic effect of poly(ethylenimine) on the transfection efficiency of galactosylated chitosan/DNA complexes." Journal of Controlled Release, vol. 105:354-366 (2005).
Kurtzman, Aaron L. et al., "Advances in directed protein evolution by recursive genetic recombination: applications to therapeutic proteins," Current Opinion in Biotechnology, vol. 12:361-370 (2001).
Lebowitz, Jonathan H. et al., "Giycosylation-independent targeting enhances enzyme delivery to lysosomes and decreases storage in mucopolysaccharidosis type VII mice," PNAS, vol. 101(9):3083-3088 (2004).
Li, Yijun et al., "Direct Multiplex Assay of Lysosomal Enzymes in Dried Blood Spots for Newborn Screening," Clinical Chemistry, vol. 50:1785-1796 (2004).
Lozier, Jay N. et al., "Efficient Transfection of Primary Cells in a Canine Hemophilia B Model Using Adenovirus-Polylysine-DNA Complexes," Human Gene Therapy, vol. 5:313-322 (1994).
Magnelli, P. et al., "A refined method for the determination of *Saccharomyces cerevisiae* cell wall composition and beta-1,6-glucan fine structure. 1," Anal. Biochem., vol. 301(1):136-150 (2002).
Martin, Brian M. et al., "Glycosylation and Processing of High Levels of Active Human Glucocerebrosidase in Invertebrate Cells Using a Baculovirus Expression Vector," DNA, vol. 7(2):99-106 (1988).
Mayo Clinic, "Rheumatoid arthritis," retrieved online at http://www.mayoclinic.com/health/rheumatoid-arthritis/DS00020Dsection=treatments-and-drugs, 3 pages, (2011.
McCaffrey, Anton P. et al., "RNA interference in adult mice," Nature, vol. 418:38-39 (2002).
Meikle, Peter J. et al., "Lysosomal storage disorders: emerging therapeutic options require early diagnosis," Eur. J. Pediatr., vol. 162:S34-S37 (2003).
Murphy, John E. et al., "A combinatorial approach to the discovery of efficient cationic peptoid reagents for gene delivery," Proc. Natl. Acad. Sci. USA, vol. 95:1517-1522 (1998).
Nakase. Hiroshi et al., "Biodegradable microspheres targeting mucosal immune-regulating cells: new approach for treatment of inflammatory bowel disease," J. Gastroenterol., vol. 38(Suppl. XV):59-62 (2003).
Nakase, Hiroshi et al., "Development of an Oral Drug Delivery System Targeting Immune-Regulating Cells in Experimental Inflammatory Bowel Disease: A New Therapeutic Strategy," The Journal of Pharmacology and Experimental Therapeutics, vol. 292(1):15-21 (2000).
Nakase, Hiroshi et al., "New Cytokine Delivery System Using Gelatin Microspheres Containing Interleukin-10 for Experimental Inflammatory Bowel Disease," The Journal of Pharmacology and Experimental Therapeutics, vol. 301 (1):59-65 (2002).
Neutra, Marian R., "Current Concepts in Mucosal Immunity V. Role of M cells in transepithelial transport of antigens and pathogens to mucosal immune system," Am. J. Physiol., vol. 274:C785-C791 (1998).
Niederman, Richard et al., "Enhanced neutrophil emigration and Porphyromonas gingivalis reduction following PGG-glucan treatment of mice," Archives of Oral Biology, vol. 47:613-618 (2002).
Niederman, R. et al., "PGG-glucan Enhances the Host Response to Periodontal Pathogens," J. Dent. Res., vol. 76:176, IADR Abstracts, Poster Presentation 1301 (1997).
NIH Guide: CNS Therapy Development for Lysosomal Storage Disorders, Department of Health and Human Services, pp. 1-12 (2004).
Novelli, Enrico M. et al., "Gene therapy for lysosomal storage disorders," Expert Opin. Bioi. Ther., vol. 1(5):857-867 (2001).
Onderdonk, Andrew B. et al., "Anti-Infective Effect of Poly-beta1-6-Giucotriosyl-betal-3-Giucopyranose Glucan In Vivo," Infection and Immunity, vol. 60(4):1642-1647 (1992).
Orvisky, Eduard et al., "Giucosylsphingosine accumulation in tissue from patients with Gaucher disease: correlation with phenotype and genotype," Molecular Genetics and Metabolism, vol. 76:262-270 (2002).
Ostroff, G.R. et al., "A New Beta-Giucan-Based Macrophage-Targeted Adjuvant," Polymeric Drugs and Drug Delivery Systems, ACS Symposium Series, Chapter 6:52-59 (1991).
Ostroff, G.R. et al., "Macrophage-Targeted Polysaccharide Microcapsules for Antigen and Drug Delivery," Polymer Preprints, vol. 31(2):200-201 (1990).
Ostroff, G.R. et al., "Molecular Cloning with Bifunctional Plasmid Vectors in Bacillus subtilis, I. Construction and Analysis of B. subtilis Clone Banks in *Escherichia coli*," Mol. Gen. Genet., vol. 193:299-305 (1984).
Ostroff, G.R. et al., "Molecular Cloning with Bifunctional Plasmid Vectors in Bacillus subtilis, II. Transfer of Sequences Propagated in *Escherichia coli* to B. subtilis," Mol. Gen. Genet., vol. 193:306-311 (1984).
Ostroff, G.R. et al., "Molecular Cloning with Bifunctional Plasmid Vectors in Bacillus subtilis: Isolation of a Spontaneous Mutant of Bacillus subtilis with Enhanced Transformability for *Escherichia coli*-Propagated Chimeric Plasmid DNA," Journal of Bacteriology, vol. 156(2):934-936 (1983).
Ostroff, Gary et al., "Potential for Beta 1,3-Giucans to Prevent and Treat Biological Warfare Infections," BTR2003: Unified Science & Technology for Reducing Biological Threats and Countering Terrorism, 13 pages (2002).
Peer, Dan et al., "Selective gene silencing in activated leukocytes by targeting siRNAs to the integrin lymphocyte function-associated antigen-1," PNAS, vol. 104(10):4095-4100 (2007).
piRES-EGFP, Vector Information, GenBank Accession#: Submission in Progress, PT3157-5, Clontech Laboratories, Inc., (1997).
Powelka, Aimee M. et al., "Suppression of oxidative metabolism and mitochondrial biogenesis by the transcriptional corepressor RIP140 in mouse adipocyles," The Journal of Clinical Investigation, vol. 116(1):125-136 (2006).
Reichner, Jonathan S. et al., "Receptor-mediated phagocylosis of rat macrophages is regulated differentially for opsonized particle and non-opsonized particles containing b-glucan," Immunology, vol. 104:198-206 (2001).
Ribeiro, C.C. et al., "Calcium phosphate-alginate microspheres as enzyme delivery matrices," Biomaterials, vol. 25:4363-4373 (2004).
Schiffelers, Raymond M. et al., "Effects of Treatment With Small Interfering RNA on Joint Inflammation in Mice With Collagen-Induced Arthritis," Arthritis & Rheumatism, vol. 52(4):1314-1318 (2005).

(56) References Cited

OTHER PUBLICATIONS

Selitrennikoff, Claude P. et al., "Emerging therapeutic cell wall targets in fungal infections," Emerging Therapeutic Targets, vol. 3(1):53-72 (1999).
Shetty, K. et al., "Gene therapy of hepatic diseases: prospects for the new millennium," Gut, vol. 46:136-139 (2000).
Shoelson, Steven E. et al., "Inflammation and insulin resistance," The Journal of Clinical Investigation, vol. 116 (7):1793-1801 (2006).
Simon, Ethan S. et al., "Preparation of Cylidine 5'-Monophospho-N-Acetylneuraminic Acid and Uridine 5'-Diphosphoglucuronic Acid; Syntheses of alpha-2, 6-Sialyllactosamine, alpha-2, 6-Sialyllactose, and Hyaluronic Acid," Methods in Enzymology, vol. 179:275-287 (1989).
Sleeper, M.M. et al., "Gene Therapy Ameliorates Cardiovascular Disease in Dogs With Mucopolysaccharidosis VII," Circulation, vol. 110:815-820 (2004).
Song, Erwei et al., "Antibody mediated in vivo delivery of small interfering RNAs via cell-surface receptors," Nature Biotechnology, vol. 23(6):709-717 (2005).
Sorensen, Dag R. et al., "Gene Silencing by Systemic Delivery of Synthetic siRNAs in Adult Mice," J. Mol. Bioi., vol. 327:761-766 (2003).
Soto, Ernesto R. et al., "Characterization of Multilayered Nanoparticles Inside Yeast Cell Wall Particles for DNA Delivery," Bioconjugate Chemistry, vol. 19(4):840-848 (2008).
Soto, Ernesto et al., "Giucan Particle Encapsulated Rifampicin for Targeted Delivery to Macrophages," Polymers, vol. 2:681-689 (2010).
Soto, E. et al., "Glucan Particles as an Efficient siRNA Delivery Vehicle," Nanotech 2008, vol. 2, Chapter 4, pp. 332-335 (2008).
Soto, Ernesto R. et al., "Glucan Particles for Macrophage Targeted Delivery of Nanoparticles," Journal of Drug Delivery, vol. 2012, 13 pages (2011).
Soto. E. et al.. "Oral Macrophage Mediated Gene Delivery System," NSTI-Nanotech, vol. 2:378-381 (2007).
Soto, Ernesto R. et al., "Yeast Cell Wall Particles as a Versatile Macromolecular Delivery System," Polymeric Materials: Science & Engineering, vol. 98:591-593 (2008).
Soutschek, Jurgen et al., "Therpeutic silencing of an endogenous gene by systemic administration of modified siRNAs," Nature, vol. 432:173-178 (2004).
Stashenko, P. et al., "Reduction of Infection-stimulated Periapical Bone Resorption by the Biological Response Modifier PGG Glucan," J. Dent. Res., vol. 74(1):323-330 (1995).
Tang, Xiaoqing et al., "An RNA interference-based screen identifies MAP4K4/NIK as a negative regulator of PPARgamma, adipogenesis, and insulin-responsive hexose transport," PNAS, vol. 103(7):2087-2092 (2006).
Tesz, Gregory J. et al., "Glucan particles for selective delivery of siRNA to phagocytic cells in mice," Biochem. J., vol. 436:351-362 (2011).
Tesz, Gregory J. et al., "Tumor Necrosis Factor alpha (TNFalpha) Stimulates Map4k4 Expression through TNFalpha Receptor 1 Signaling to c-Jun and Activating Transcription Factor 2," The Journal of Biological Chemistry, vol. 282 (27):19302-19312 (2007).
Trubetskoy, Vladimir S. et al., "Quantitative Assessment of DNA Condensation," Analytical Biochemistry, vol. 267:309-313 (1999).
Trubetskoy, V.S. et al., "Recharging cationic DNA complexes with highly charged polyanions for in vitro and in vivo gene delivery," Gene Therapy, vol. 10:261-271 (2003).
Tsuji, Shoji et al., "Signal sequence and DNA-mediated expression of human lysosomal a-galactosidase A," Eur. J. Biochem., vol. 165:275-280 (1987).
Uematsu, T. et al., "Increased Infection Resistance in PGG-glucan-Treated ICAM-1 Deficient Mice," J. Dent. Res., vol. 76:176, IADR Abstracts, Poster Presentation 1302 (1997).
Van Der Lubben, I.M. et al., "Transport of Chitosan Microparticles for Mucosal Vaccine Delivery in a Human Intestinal M-cell Model," Journal of Drug Targeting, vol. 10(6):449-456 (2002).

Vetvicka, Vaclav et al., "Pilot Study: Orally-Administered Yeast Beta1,3-glucan Prophylactically Protects Against Anthrax Infection and Cancer in Mice," JANA, vol. 5(2):5-9 (2002).
Wesche-Soldato, Doreen E. et al., "In vivo delivery of caspase-8 or Fas siRNA improves the survival of septic mice," Blood, vol. 106(7):2295-2301 (2005).
Wilcox, William R., "Lysosomal Storage Disorders: The Need for Better Pediatric Recognition and Comprehensive Care," J. Pediatr., vol. 144:S3-S14 (2004).
Williams, William V. et al., "Restricted Heterogeneity ofT Cell Receptor Transcripts in Rheumatoid Synovium," J. Clin. Invest., vol. 90:326-333 (1992).
Wilson, H.M. et al., "Targeting Genetically Modified Macrophages to the Glomerulus," Nephron Exp. Nephrol., vol. 94:e113-e118 (2003).
Wu, George Y., et al., "Receptor-mediated in Vitro Gene Transformation by a Soluble DNA Carrier System," The Journal of Biological Chemistry, vol. 262(10):4429-4432 (1987).
Young, Shih-Houng et al., "A Comparison of the Pulmonary Inflammatory Potential of Different Components of Yeast Cell Wall," Journal of Toxicology and Environmental Health, Part A, vol. 70:1116-1124 (2007).
Zhao, H. et al., "Protein Glycoengineering," Journal of Chinese Biotechnology, vol. 23(9):18-20 (2003).
Zimmermann, TracyS. et al., "RNAi-mediated gene silencing in non-human primates," Nature, vol. 441:111-114 (2006).
Zimmerman, Janet W. et al., "A Novel Carbohydrate-Giycosphingolipid Interaction between a b-(1-3)-Giucan Immunomodulator, PGG-glucan, and Lactosylceramide of Human Leukocytes," The Journal of Biological Chemistry, vol. 273(34):22014-22020 (1998).
Australian Office Action for Application No. 2005284727, dated Apr. 13, 2010.
Chinese Office Action for Application No. 200580037576.4, dated Mar. 23, 2010.
International Search Report and Written Opinion for Application No. PCT/US2008/081653, dated Nov. 10, 2009.
International Search Report for Application No. PCT/US2005/021161, dated Jul. 25, 2006.
International Search Report for Application No. PCT/US2005/033300.
Japanese Office Action for Application No. 2007-516687, pp. 1-4, dated Sep. 28, 2011.
First Office Action, Chinese Application for Invention No. 200580037576.4, and English translation as provided by the Chinese foreign associate.
Indian Office Action for Application No. 163/KOLNP/2007, dated Apr. 26, 2011.
Agarwal, Sarika et al., "Linkage Specificity and Role of Properdin in Activation of the Alternative Complement Pathway by Fungal Glycans," mBio, vol. 2(5):e00178, 10 pages (2011).
Aouadi, Myriam et al., "Orally delivered siRNA targeting macrophage Map4k4 suppresses systemic inflammation," Nature, vol. 458(7242):1180-1184 (2009).
Aviner, S. et al., "Anaphylactoid Reaction to Imiglucerase, but Not to Alglucerase, in a Type I Gaucher Patient," Blood Cells, Molecules, and Diseases, vol. 25(5):92-94 (1999).
Beier, Rita et al., "Kinetics of particle uptake in the domes of Peyer's patches," Am. J. Physiol., vol. 275:G130-G137 (1998).
Bell, Stacey et al., "Effect of beta-GLucan from Oats and Yeast on Serum Lipids," Critical Reviews in Food Science and Nutrition, vol. 39(2):189-202 (1999).
Bogwald, Jarl et al., "Lysosomal Glycosidases in Mouse Peritoneal Macrophages Stimulated in Vitro With Soluble and Insoluble Glycans," Journal of Leukocyte Biology, vol. 35:357-371 (1984).
Bonfils. E. et al.. "Drug targeting: synthesis and endocytosis of oligonucleotide-neoglycoprotein conjugates." Nucleic Acids Research. vol. 20(17):4621-4629 (1992).
Bonten et al. 'Targeting macrophages with baculovirus-produced lysosomal enzymes: implications for enzyme replacement therapy of the glycoprotein storage disorder galactosialidosis.' The FASEB journal 18.9 (2004): 971-973.

(56) References Cited

OTHER PUBLICATIONS

Brooks et al. "Significance of immune response to enzyme-replacement therapy for patients with a lysosomal storage disorder." Trends in molecular medicine 9.10 (2003): 450-453.

Burke, Bernard, "Macrophages as novel cellular vehicles for gene therapy," Expert Opin. Bioi. Ther., vol. 3 (6):919-924 (2003).

Burke, B. et al., "Macrophages in gene therapy: cellular delivery vehicles and in vivo targets," Journal of Leukocyte Biology, vol. 72:417-428 (2002).

Champagne, M.J. et al., "Binding of GM1-ganglioside to a synthetic peptide derived from the lysosomal sphingolipid-activator-protein saposin B," FEBS Lett., vol. 347(2-3):265-267 (1994).

Chang, P.L., "Microencapsulation—An alternative approach to gene therapy," Transfusion Science, vol. 17(1):35-43 (1996).

Charrow, Joel et al., "Enzyme Replacement Therapy and Monitoring for Children with Type 1 Gaucher Disease: Consensus Recommendations," J. Pediatr., vol. 144:112-120 (2004).

Chaudhary, Vuay K. et al., "A rapid method of cloning functional variable-region antibody genes in *Escherichia coli* as single-chain immunotoxins," Proc. Natl. Acad. Sci. USA, vol. 87:1066-1070 (1990).

Cho, Monique E. et al., "Fabry disease in the era of enzyme replacement therapy: a renal perspective," Pediatr. Nephrol., vol. 19:583-593 (2004).

Clark, M. Ann et al., "Exploiting M cells for drug and vaccine delivery," Advanced Drug Delivery Reviews, vol. 50:81-106 (2001).

Clonetech.com—piRES2-DsRed2 Vector Information, PT3663-5, Catalog #6990-1, pp. 1-3 (2002).

Curiel, David T. et al., "Adenovirus enhancement of transferrin-polylysine-mediated gene delivery," Proc. Natl. Acad. Sci. USA, vol. 88:8850-8854 (1991).

D'Azzo, Alessandro et al., "Gene Transfer Strategies for Correction of Lysosomal Storage Disorders," Acta Haematol., vol. 110:71-85 (2003).

Dervan, Peter B., "Molecular Recognition of DNA by Small Molecules," Bioorganic & Medicinal Chemistry, vol. 9:2215-2235 (2001).

Desnick, Robert J. et al., "Fabry Disease, an Under-Recognized Multisystemic Disorder: Expert Recommendations for Diagnosis, Management, and Enzyme Replacement Therapy," Ann. Intern Med., vol. 138:338-346 (2003).

Donzelli, Bruno Giuliano Garisto et al., "Enhanced enzymatic hydrolysis of langostino shell chitin with mixtures of enzymes from bacterial and fungal sources," Carbohydrate Research, vol. 338:1823-1833 (2003).

Egan, William et al., "Evaluation of Polysaccharides," Characterization of Biotechnology Pharmaceutical Products. Dev. Biol. Stand., Brown, F. (Ed.), Karger, vol. 96, pp. 155-156 (1998).

El-Gabalawy, Hani S. et al., "Why do we not have a cure for rheumatoid arthritis?" Arthritis Res., vol. 4(Suppl. 3): S297-S301 (2002).

Erbacher, Patrick et al., "Chitosan-Based Vector/DNA Complexes for Gene Delivery: Biophysical Characteristics and Transfection Ability," Pharmaceutical Research, vol. 15(9):1332-1339 (1998).

\* cited by examiner

Yeast Cell Wall Particle
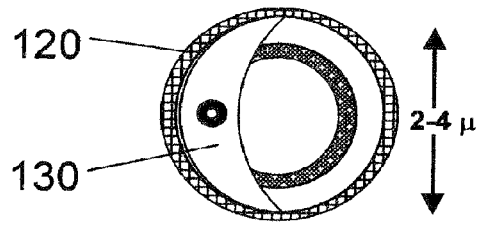
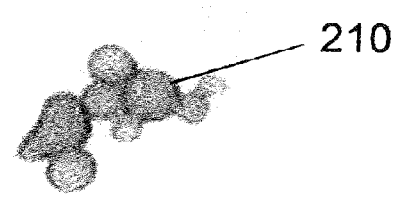
Figure 2A          Figure 2B
YGMP Beta Glucan
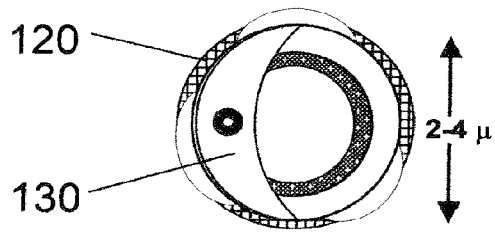
Figure 2C          Figure 2D
YGP Beta Glucan
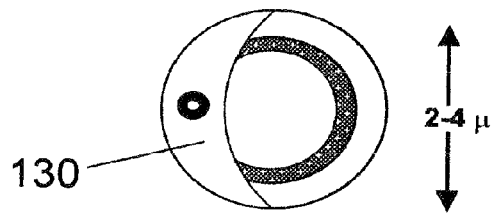
Figure 2E          Figure 2F

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(1)
<223> OTHER INFORMATION: fluorescein

<400> SEQUENCE: 1
ttggtcatcc atggctct                                                        18

<210> SEQ ID NO 2
<211> LENGTH: 21
<212> TYPE: DNA
<213> ORGANISM: Artificial sequence
<220> FEATURE:
<223> OTHER INFORMATION: Description of Artificial Sequence:  Synthetic
      RNAi control oligonucleotide
<220> FEATURE:
<221> NAME/KEY: misc_feature
<222> LOCATION: (1)..(1)
<223> OTHER INFORMATION: fluorescein
<220> FEATURE:
<221> NAME/KEY: misc_feature
<222> LOCATION: (20)..(21)
<223> OTHER INFORMATION: Deoxythymidine

<400> SEQUENCE: 2
uucuccgaac gugucacgut t                                                    21
```

DRUG DELIVERY PRODUCT AND METHODS

RELATED APPLICATIONS

This application is a continuation of U.S. patent application Ser. No. 12/781,549, filed May 17, 2010, which is a continuation of U.S. patent application Ser. No. 10/869,693, filed Jun. 16, 2004, (now U.S. Pat. No. 7,740,861). The entire contents of these applications are incorporated herein by reference.

BACKGROUND OF THE INVENTION

Drug delivery systems are designed to provide a biocompatible reservoir of an active agent for the controlled release of the active agent dependent either on time, or on local conditions, such as pH. While macroscopic drug delivery systems such as transdermal patches, implantable osmotic pumps and implantable subcutaneous depots (e.g., NOR-PLANT™) have had some success, there has been continuing interest in microscopic drug delivery systems such as microcapsules, microparticles and liposomes.

Microcapsules and microspheres are usually powders consisting of spherical particles 2 millimeters or less in diameter, usually 500 microns or less in diameter. If the particles are less than 1 micron, they are often referred to as nanocapsules or nanospheres. A description of methods of making and using microspheres and microcapsules can be found, for example in U.S. Pat. No. 5,407,609. Microcapsules and microspheres can be distinguished from each other by whether the active agent is formed into a central core surrounded by an encapsulating structure, such as a polymeric membrane, or whether the active agent is dispersed throughout the particle; that is, the internal structure is a matrix of the agent and excipient, usually a polymeric excipient. The release of the active agent from a microcapsule is often regulated by the biodegradation of the matrix material, usually a biodegradable polymeric material such as either poly(DL-lactide) (DL-PL) or poly(DL-lactide-co-glycolide) (DL-PLG) as the polymeric excipient.

Liposomes can be considered microcapsules in which the active agent core is encompassed by a lipid membrane instead of a polymeric membrane. Liposomes are artificial lipid vesicles consisting of lipid layers, where the antigen may be encapsulated inside the aqueous compartment of the liposome, or associated with the antigen on the surface via surface-coupling techniques. Liposomes can be prepared easily and inexpensively on a large scale and under conditions that are mild to entrapped antigens. They do not induce immune responses to themselves, and are used in humans for parenterally administered drugs.

While the high surface area/volume ratio of microcapsules, microspheres and liposomes favor the release of the active agent, their small size provides challenges in manufacturing. A wide variety of methods to prepare microcapsules and microspheres are described in the literature, e.g., U.S. Pat. No. 5,407,609. Several of these methods make use of emulsions to make microspheres, in particular to make microspheres less than 2 millimeters in diameter. To give a general example of such processes, one can dissolve a polymer in a suitable organic solvent (the polymer solvent), dissolve or disperse an agent in this polymer solution, disperse the resulting polymer/agent mixture into an aqueous phase (the processing medium) to obtain an oil-in-water emulsion with oil microdroplets dispersed in the processing medium, and remove the solvent from the microdroplets to form microspheres. These processes can also be performed with water-in-oil emulsions and with double emulsions. The use of emulsion-based processes that follow this basic approach is described in several U.S. patents, such as U.S. Pat. Nos. 3,737,337, 3,891,570, 4,384,975, 4,389,330, and 4,652,441.

Alternatively, extracted yeast cell wall particles are readily available, biodegradable, substantially spherical particles about 2-4 µm in diameter. Preparation of extracted yeast cell wall particles is known in the art, and is described, for example in U.S. Pat. Nos. 4,992,540, 5,082,936, 5,028,703, 5,032,401, 5,322,841, 5,401,727, 5,504,079, 5,968,811, 6,444,448 B1, 6,476,003 B1, published U.S. applications 2003/0216346 A1, 2004/0014715 A1, and PCT published application WO 02/12348 A2. A form of extracted yeast cell wall particles, referred to as "whole glucan particles," have been suggested as delivery vehicles, but have been limited either to release by simple diffusion of active ingredient from the particle or release of an agent chemically crosslinked to the whole glucan particle by biodegradation of the particle matrix. See U.S. Pat. Nos. 5,032,401 and 5,607,677.

Extracted yeast cell wall particles, primarily due to their beta-glucan content, are targeted to phagocytic cells, such as macrophages and cells of lymphoid tissue. The mucosal-associated lymphoid tissue (MALT) comprises all lymphoid cells in epithelia and in the lamina propria lying below the body's mucosal surfaces. The main sites of mucosal-associated lymphoid tissues are the gut-associated lymphoid tissues (GALT), and the bronchial-associated lymphoid tissues (BALT).

Another important component of the GI immune system is the M or microfold cell. M cells are a specific cell type in the intestinal epithelium over lymphoid follicles that endocytose a variety of protein and peptide antigens. Instead of digesting these proteins, M cells transport them into the underlying tissue, where they are taken up by local dendritic cells and macrophages.

M cells take up molecules and particles from the gut lumen by endocytosis or phagocytosis. This material is then transported through the interior of the cell in vesicles to the basal cell membrane, where it is released into the extracellular space. This process is known as transcytosis. At their basal surface, the cell membrane of M cells is extensively folded around underlying lymphocytes and antigen-presenting cells, which take up the transported material released from the M cells and process it for antigen presentation.

A study has shown that transcytosis of yeast particles (3.4+/−0.8 micron in diameter) by M cells of the Peyer's patches takes less than 1 hour (Beier, R., & Gebert, A., Kinetics of particle uptake in the domes of Peyer's patches, Am J Physiol. 1998 July; 275(1 Pt 1):G130-7). Without significant phagocytosis by intraepithelial macrophages, the yeast particles migrate down to and across the basal lamina within 2.5-4 hours, where they quickly get phagocytosed and transported out of the Peyer's patch domes. M cells found in human nasopharyngeal lymphoid tissue (tonsils and adenoids) have been shown to be involved in the sampling of viruses that cause respiratory infections. Studies of an in vitro M cells model have shown uptake of fluorescently labeled microspheres (Fluospheres, 0.2 µm) and chitosan microparticles (0.2 µm) van der Lubben I. M., et al., Transport of chitosan microparticles for mucosal vaccine delivery in a human intestinal M-cell model, J Drug Target, 2002 September; 10(6):449-56. A lectin, *Ulex europaeus* agglutinin 1 (UEA1, specific for alpha-L-fucose residues) has been used to target either polystyrene microspheres (0.5 nm) or polymerized liposomes to M cells (0.2 µm) (Clark, M. A., et al., Targeting polymerised liposome vaccine carriers to intestinal M cells, Vaccine. 2001 Oct. 12; 20(1-2): 208-17). In vivo studies in mice have reported that poly-D, L-lactic acid (PDLLA) microspheres or gelatin microspheres (GM) can be efficiently taken up by macrophages and M cells. (Nakase, H., et al., Biodegradable microspheres targeting mucosal immune-regulating cells: new approach for treatment of inflammatory bowel disease, J. Gastroenterol. 2003 March; 38 Suppl 15:59-62).

However, it has been reported that uptake of synthetic particulate delivery vehicles including poly(DL-lactide-co-glycolide) microparticles and liposomes is highly variable, and is determined by the physical properties of both particles and M cells. Clark, M. A., et al., Exploiting M cells for drug and vaccine delivery, Adv Drug Deliv Rev. 2001 Aug. 23; 50(1-2):81-106. The same study reported that delivery may be enhanced by coating the particles or liposomes with reagents including appropriate lectins, microbial adhesins and immunoglobulins which selectively bind to M cell surfaces. See also, Florence, A. T., The oral absorption of micro- and nanoparticulates: neither exceptional nor unusual, Pharm Res. 1997 March; 14(3):259-66.

Pathogen pattern recognition receptors (PRRs) recognize common structural and molecular motifs present on microbial surfaces and contribute to induction of innate immune responses. Mannose receptors and beta-glucan receptors in part participate in the recognition of fungal pathogens. The mannose receptor (MR), a carbohydrate-binding receptor expressed on subsets of macrophages, is considered one such PRR. Macrophages have receptors for both mannose and mannose-6-phosphate that can bind to and internalize molecules displaying these sugars. The molecules are internalized by endocytosis into a pre-lysosomal endosome. This internalization has been used to enhance entry of oligonucleotides into macrophages using bovine serum albumin modified with mannose-6-phosphate and linked to an oligodeoxynucleotide by a disulfide bridge to a modified 3' end; see Bonfils, E., et al., Nucl. Acids Res. 1992 20, 4621-4629. see E. Bonfils, C. Mendes, A. C. Roche, M. Monsigny and P. Midoux, Bioconj. Chem., 3, 277-284 (1992). Macrophages also express beta-glucan receptors, including CR3 (Ross, G. D., J. A. Cain, B. L. Myones, S. L. Newman, and P. J. Lachmann. 1987. Specificity of membrane complement receptor type three ($CR_3$) for β-glucans. *Complement Inflamm.* 4:61), dectin-1. (Brown, G. D. and S. Gordon. 2001. Immune recognition. A new receptor for β-glucans. *Nature* 413:36), and lactosylceramide (Zimmerman J W, Lindermuth J, Fish P A, Palace G P, Stevenson T T, DeMong D E. A novel carbohydrate-glycosphinglipid interaction between a beta-(1-3)-glucan immunomodulator, PGG-glucan, and lactosylceramide of human leukocytes. J Biol. Chem. 1998 Aug. 21:273(34):22014-20). The beta-glucan receptor, $CR_3$ is predominantly expressed on monocytes, neutrophils and NK cells, whereas dectin-1 is predominantly expressed on the surface of cells of the macrophages. Lactosylceramide is found at high levels in M cells. Microglia can also express a beta-glucan receptor (Muller, C. D., et al. Functional beta-glucan receptor expression by a microglial cell line, Res Immunol. 1994 May; 145(4):267-75).

There is evidence for additive effects on phagocytosis of binding to both mannose and beta-glucan receptors. Giaimis et al. reported observations suggesting that phagocytosis of unopsonized heat-killed yeast (*S. cerevisiae*) by murine macrophage-like cell lines as well as murine peritoneal resident macrophages is mediated by both mannose and beta-glucan receptors. To achieve maximal phagocytosis of unopsonized heat-killed yeast, coexpression of both mannose and beta-glucan receptors is required (Giaimis, J., et al., Both mannose and beta-glucan receptors are involved in phagocytosis of unopsonized, heat-killed *Saccharomyces cerevisiae* by murine macrophages, J Leukoc Biol. 1993 December; 54(6):564-71).

SUMMARY OF THE INVENTION

In a preferred embodiment, the present invention provides a particulate delivery system comprising an extracted yeast cell wall comprising beta-glucan and a payload trapping molecule. The particulate delivery system optionally, but typically, also includes a payload molecule, wherein the payload molecule and the payload trapping molecule are soluble in the same solvent system. In preferred embodiments, the solvent system comprises water. In other preferred embodiments, the solvent system consists essentially of water. The particulate delivery system of the present invention is useful for both in vivo and in vitro delivery of payload molecules to cells.

In particularly preferred embodiments, extracted yeast cell wall comprises less than 90 weight percent beta-glucan. In certain preferred embodiments, the extracted yeast cell wall comprises more than 50 weight percent chitin. In other preferred embodiments, the extracted yeast cell wall further comprises more than 30 weight percent mannan. In certain embodiments, the extracted yeast cell wall includes more than 1 weight percent protein.

In preferred embodiments, the payload molecule is selected from the group consisting of a polynucleotide, a peptide, a protein, a small organic active agent, a small inorganic active agent and a mixture thereof. In certain preferred embodiments, the payload molecule is a polynucleotide selected from the group consisting of an oligonucleotide, an antisense construct, a siRNA, an enzymatic RNA, a recombinant DNA construct, an expression vector, and a mixture thereof. In other preferred embodiments, the particulate delivery system of the present invention is useful for in vivo or in vitro delivery of payload molecules such as amino acids, peptides and proteins. The peptides can be signaling molecules such as hormones, neurotransmitters or neuromodulators, and can be the active fragments of larger molecules, such as receptors, enzymes or nucleic acid binding proteins. The proteins can be enzymes, structural proteins, signaling proteins or nucleic acid binding proteins, such as transcription factors.

In other preferred embodiments, the payload molecule is a small organic active agent, such as a therapeutic agent or a diagnostic agent. In particularly preferred embodiments, the small organic active agent is a sequence-specific DNA binding oligomer, more preferably an oligomer of heterocyclic polyamides that bind to the minor groove of double stranded DNA, such as those disclosed in U.S. Pat. No. 6,506,906 and in Dervan, P. Molecular Recognition of DNA by Small Molecules, Bioorganic & Medicinal Chemistry (2001) 9: 2215-2235, both of which are hereby incorporated by reference. In preferred embodiments, the oligomer has monomeric subunits selected from the group consisting of N-methylimidazole carboxamide, N-methylpyrrole carboxamide, beta-alanine and dimethylaminopripylamide.

In other preferred embodiments, the particulate delivery system of the present invention includes inorganic active agents, e.g., gastrointestinal therapeutic agents such as aluminum hydroxide, calcium carbonate, magnesium carbonate, sodium carbonate and the like.

The choice of the payload trapping molecule can confer specific characteristics to the particulate delivery system. In general, the preferred payload trapping molecule is biocompatible and pharmaceutically acceptable. As noted above, the payload molecule and the payload trapping molecule are soluble in the same solvent system. Suitable payload trapping molecules include natural and synthetic polymers. In certain embodiments, the physical characteristics of the payload trapping molecule, such as agarose or polyacrylamide, provide useful advantages Suitable polymers include polysaccharides. In preferred embodiments, the polysaccharide selected is from the group consisting of agarose, an alginate, a xanthan, a dextran, a chitosan, a galactomannan gum, a derivative thereof and a mixture thereof. In certain preferred embodiments, the polysaccharides have been derivatized to produce cationic or anionic characteristics at physiological pH.

In other embodiments, the payload trapping molecule is a charged molecule at physiological pH, such as a cationic polymer, an anionic polymer, a cationic detergent, an anionic detergent and a mixture thereof. Preferred cationic polymers include chitosan, poly-L-lysine and polyethylenimines (PEIs), including substantially linear polyethylenimines, such as JetPEI, a commercially available linear polyethylenimine cationic polymer transfection reagent (Qbiogene, Inc., CA). Other cationic polymer transfection reagents are also suitable, preferably CytoPure™, a proprietary, commercially available, water-soluble cationic polymer transfection reagent (Qbiogene, Inc., CA). In other preferred embodiments, suitable anionic polymers include alginates, dextrans and xanthans, including derivatized alginates, dextrans and xanthans. In further preferred embodiments, the payload trapping molecule is a cationic detergent such as hexadecyltrimethylammoniumbromide. In one preferred embodiment, a mixture of a cationic detergent, such as hexadecyltrimethylammoniumbromide, and a cationic polymer, such as a polyethylenimine, is used. In another preferred embodiment, a mixture of a cationic detergent, such as hexadecyltrimethylammoniumbromide, and a cationic polymer, such as chitosan or PEI, can be used.

While not being held to a single hypothesis, it is believed that, in addition to facilitating the retention of the payload by the yeast cell wall particles, a preferred payload trapping molecule serves to encourage the release of the payload molecule from the endosome of a phagocytic cell by acting as a detergent, by helping to swell the endosome osmotically, or by other effects.

In other preferred embodiments, the present invention provides methods of using the particulate delivery system. In certain preferred embodiments, the invention provides methods of delivering a payload molecule to a cell comprising the steps of providing a extracted yeast cell wall comprising beta-glucan, the yeast cell wall defining an internal space; contacting the extracted yeast cell wall with a payload molecule wherein the payload molecule becomes at least partially enclosed within the internal space; contacting the extracted yeast cell wall with a payload trapping molecule wherein the payload trapping molecule at least partially confines the payload molecule within the extracted yeast cell wall to form a particulate delivery system; and contacting a cell with the particulate delivery system. Preferably the method further includes the step of internalizing the particulate delivery system by the cell.

In other preferred embodiments, the invention provides methods of making a particulate delivery system comprising the steps of providing a extracted yeast cell wall comprising beta-glucan, the yeast cell wall defining an internal space; contacting the extracted yeast cell wall with a payload molecule wherein the payload molecule becomes associated with the extracted yeast cell wall; contacting the extracted yeast cell wall with a payload trapping molecule wherein the payload trapping molecule stabilizes the association of the payload molecule with the extracted yeast cell wall to form a particulate delivery system. In preferred embodiments, the method also includes the steps of washing and drying the particulate delivery system.

In other preferred embodiments, the present invention provides methods of exposing an individual to an antigen comprising the step of contacting a phagocytic cell of the individual with a particulate delivery system comprising an extracted yeast cell wall comprising beta-glucan, a payload trapping molecule and payload molecule, wherein the payload molecule is a polynucleotide comprising a control element operatively linked to an open reading frame encoding a peptide that can be controllably expressed in the cells of the individual. Preferably the encoded peptide is an antigenic peptide. In further preferred embodiments, the present invention provides methods of exposing an individual to an antigen comprising the step of contacting a phagocytic cell of the individual with a particulate delivery system comprising an extracted yeast cell wall comprising beta-glucan, a payload trapping molecule and payload molecule, wherein the payload molecule is a antigenic molecule. A preferred antigenic molecule is a toxoid.

In preferred embodiments, the contacted cells are macrophages, but may also include any cell capable of yeast particle phagocytosis, including M cells of the Peyer's patches, monocytes, neutrophils, dendritic cells, Langerhans cells, Kupffer cells, alveolar phagocytes, peritoneal macrophages, milk macrophages, microglia, eosinophils, granulocytes, mesengial phagocytes, synovial A cells and other phagocytes. In preferred embodiments, the particulate delivery system is administered orally and absorbed via M cells of the Peyer's patches in the gut.

In preferred embodiments the polynucleotide is a recombinant DNA construct comprising a control element operatively linked to an open reading frame encoding a protein, e.g. an expression vector. The protein can be a structural protein, a protein having enzymatic activity, a membrane protein a DNA binding protein or a signaling protein. In certain preferred embodiments, the protein is an antigenic protein.

In certain preferred embodiments, the method further includes the step of the cell expressing the protein. The expressed protein can be retained intracellularly by the cell, incorporated in a membranous structure, such as the plasma membrane, or be secreted by the cell.

In other embodiments, more than one type of polynucleotide is enclosed within the particulate delivery system. In preferred embodiments, the polynucleotides provide the ability to express multiple gene products under control. In certain embodiments, at least one expressible gene product is a membrane protein, preferably a membrane receptor, most preferably a membrane-bound receptor for a signaling molecule. In some embodiments, at least one expressible gene product is a soluble protein, preferably a secreted protein, most preferably a signaling protein or peptide.

In other embodiments, the present invention provides a method of delivering a drug to a macrophage cell including the steps of providing a substantially spherical extracted yeast cell wall comprising beta-glucan, the yeast cell wall defining an internal space; contacting the extracted yeast cell wall with a drug wherein the drug is at least partially enclosed within the internal space; contacting the extracted yeast cell wall with a trapping molecule wherein the trapping molecule is at least partially enclosed within the internal space to form a particulate drug delivery system; and contacting a macrophage cell with the particulate drug delivery system. Preferably, the method also includes the step of internalizing the particulate drug delivery system by the macrophage. In preferred embodiments, the method also includes the step of transporting the particulate drug delivery system by the macrophage. In particularly preferred embodiments, the macrophage delivers the particulate drug delivery system to a macrophage-attracting site, such as a site of infection, inflammatory reaction, hypoxia or hyperplasia. In certain preferred embodiments, the macrophage delivers the particulate drug delivery system to a tumor. In particularly preferred embodiments, the method includes the step of releasing the drug from the particulate drug delivery system, more preferably further including the step of releasing the drug into the extracellular space. In certain embodiments, the step of releasing the drug includes the steps of expressing a recombinant protein and secreting the protein into the extracellular space.

The present invention provides a method of immunizing an individual against a pathogen. The method comprises the step of contacting cells of said individual with a particulate delivery system comprising an extracted yeast cell wall comprising beta, glucan, a payload trapping molecule and a nucleic acid composition, thereby administering to the cells a nucleic acid molecule that comprises a nucleotide sequence that encodes a peptide which comprises at least an epitope identical to, or substantially similar to an epitope displayed on said pathogen as antigen, and said nucleotide sequence is operatively linked to regulatory sequences, wherein the nucleic acid molecule is capable of being expressed in the cells of the individual.

In another preferred embodiment, the present invention provides a method of producing immunity to a toxoid comprising the steps of providing a particulate delivery system comprising an extracted yeast cell wall comprising beta-glucan, a payload trapping molecule and a toxoid, contacting a phagocytic cell with the particulate delivery system and inducing phagocytosis of the particulate delivery system. The phagocytic cell can be one or more of macrophages, M cells of the Peyer's patches, monocytes, neutrophils, dendritic cells, Langerhans cells, Kupffer cells, alveolar phagocytes, peritoneal macrophages, milk macrophages, microglia, eosinophils, granulocytes, mesengial phagocytes, and synovial A cells.

The present invention provides methods of immunizing an individual against a hyperproliferative disease or an autoimmune disease. The methods comprise the step of contacting cells of said individual with a particulate delivery system comprising an extracted yeast cell wall comprising beta-glucan, a payload trapping molecule which includes a nucleic acid composition, thereby administering to the cells a nucleic acid molecule that comprises a nucleotide sequence that encodes a peptide which comprises at least an epitope identical to, or substantially similar to an epitope displayed on a hyperproliferative disease-associated protein or an autoimmune disease-associated protein, respectively, and is operatively linked to regulatory sequences, wherein the nucleic acid molecule is capable of being expressed in the cells of the individual.

The present invention also provides methods of treating an individual suffering from an autoimmune disease comprising the steps of contacting cells said individual with a particulate delivery system comprising an extracted yeast cell wall comprising beta-glucan, a payload trapping molecule which includes a nucleic acid composition, thereby administering to the cells a nucleic acid molecule that comprises a nucleotide sequence that restores the activity of an absent, defective or inhibited gene, or that encodes a protein that produces a therapeutic effect in the individual, and is operatively linked to regulatory sequences; the nucleic acid molecule being capable of being expressed in said cells.

In further embodiments, the present invention provides a method of immunizing an individual against a hyperproliferative disease comprising the step of contacting cells of said individual with a particulate delivery system comprising an extracted yeast cell wall comprising beta-glucan, a payload trapping molecule and a payload molecule that is a polynucleotide comprising a control sequence operatively linked to an open reading frame encoding a peptide that comprises an epitope identical to, or substantially similar to, an epitope displayed on a hyperproliferative disease-associated protein, wherein encoded peptide is capable of being expressed in the cells of the individual. In other embodiments, the present invention provides a method of treating an individual suffering from a genetic disease comprising the step of contacting cells of said individual with a particulate delivery system comprising an extracted yeast cell wall comprising beta-glucan, a payload trapping molecule and a payload molecule that is a polynucleotide thereby administering to the cells a polynucleotide that comprises a nucleotide sequence that restores the activity of an absent, defective or inhibited gene. Preferably, the polynucleotide comprises a regulatory sequence operatively linked to an open reading frame encoding a protein that produces a therapeutic effect in the individual, the protein being capable of being expressed in said cells.

The present invention also relates to methods of treating an individual suffering from an autoimmune disease comprising the steps of contacting cells said individual with a particulate delivery system comprising an extracted yeast cell wall comprising beta-glucan, a payload trapping molecule which includes a nucleic acid composition, thereby administering to the cells a nucleic acid molecule that comprises a nucleotide sequence that restores the function of an absent, defective or inhibited gene, or that encodes a protein that produces a therapeutic effect in the individual, and is operatively linked to regulatory sequences; the nucleic acid molecule being capable of being expressed in said cells.

Accordingly the present invention provides compositions and methods which prophylactically and/or therapeutically immunize an individual against a pathogen or abnormal, disease-related cell. The genetic material encodes a peptide or protein that shares at least an epitope with an immunogenic protein found on the pathogen or cells to be targeted. The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunizing includes both methods of protecting an individual from pathogen challenge, or occurrence or proliferation of specific cells, as well as methods of treating an individual suffering from pathogen infection, hyperproliferative disease or autoimmune disease. Thus, the present invention is useful to elicit broad immune responses against a target protein, i.e. proteins specifically associated with pathogens or the individual's own "abnormal" cells.

The present invention is also useful in combating hyperproliferative diseases and disorders such as cancer, by eliciting an immune response against a target protein that is specifically associated with the hyperproliferative cells. The present invention is further useful in combating autoimmune diseases and disorders by eliciting an immune response against a target protein that is specifically associated with cells involved in the autoimmune condition.

The present invention also provides pharmaceutical kits that comprise a container comprising a payload molecule selected from the group consisting of a nucleic acid composition, protein composition, small organic molecule and mixtures thereof, and a container comprising a yeast cell wall particle and a trapping molecule. Optionally, there is included in such kits excipients, carriers, preservatives and vehicles of the type described above with respect to pharmaceutical compositions. The term pharmaceutical kit is also intended to include multiple inoculants used in the methods of the present invention. Such kits include separate containers comprising different inoculants and transfer moieties. The pharmaceutical kits in accordance with the present invention are also contemplated to include a set of inoculants used in the treatment and immunizing methods and/or therapeutic methods, as described above.

The compositions and methods of the present invention are useful in the fields of both human and veterinary medicine. Accordingly, the present invention relates to genetic immunization and therapeutic treatment of mammals, birds and fish. The methods of the present invention can be particularly useful for genetic immunization and therapeutic treatment of mammalian species including human, bovine, ovine, porcine, equine, canine and feline species.

The foregoing and other features and advantages of the particulate drug delivery system and methods will be apparent from the following more particular description of preferred embodiments of the system and method as illustrated in the accompanying drawings in which like reference characters refer to the same parts throughout the different views.

BRIEF DESCRIPTION OF THE DRAWINGS

FIG. 2A is a diagram of the structure of a yeast cell wall particle; FIG. 2B is a reversed contrast (negative) grayscale image of a color fluorescence photomicrograph showing staining of the mannan component of the yeast cell wall particles by concanavalin-A-FITC (con-A-fluorescein isothiocyanate, Sigma Chemical, St. Louis, Mo.) showing substantially completely stained yeast cell wall particles 210; FIG. 2C is a diagram of the structure of a YGMP beta glucan-mannan particle, FIG. 2D is a reversed contrast (negative) grayscale image of a color fluorescence photomicrograph showing patchy con-A-FITC staining of a YGMP beta glucan-mannan particle 220; FIG. 2E is a diagram of the structure of a YGP beta glucan particle and FIG. 2F is a reversed contrast (negative) grayscale image of a color fluorescence micrograph showing the absence of con-A-FITC staining.

Figure 1:
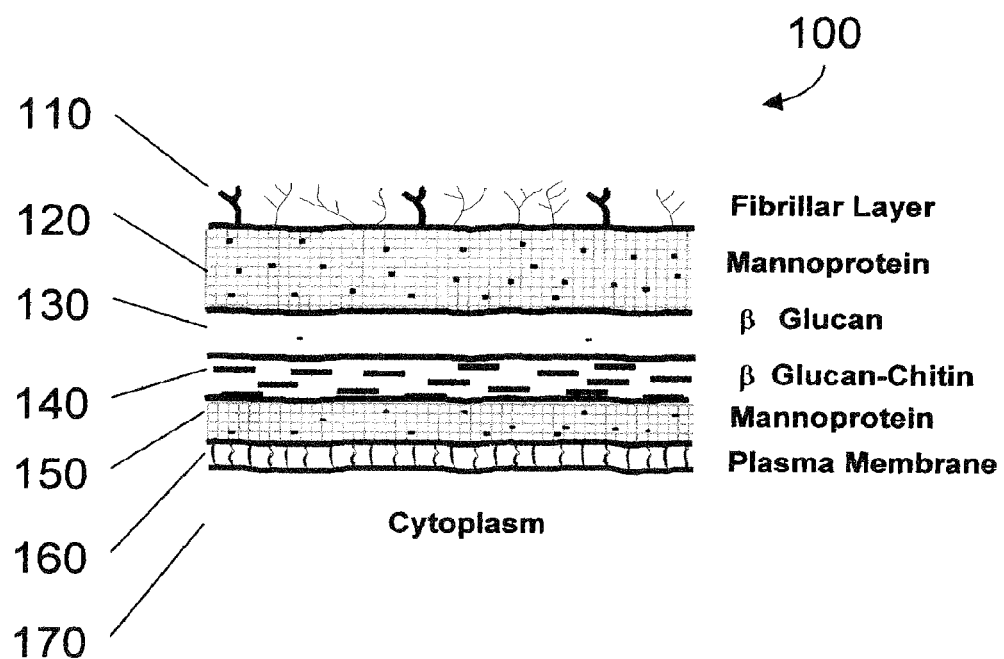
FIG. 1 is a schematic diagram 100 of a transverse section of a yeast cell wall, showing, from outside to inside, an outer fibrillar layer 110, an outer mannoprotein layer 120, a beta glucan layer 130, a beta glucan-chitin layer 140, an inner mannoprotein layer 150, the plasma membrane 160 and the cytoplasm 170.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

In preferred embodiments, the invention provides a particulate delivery system comprising an extracted yeast cell wall particle and at least one payload trapping molecule. Preferably, the yeast cell wall particle is a 2-4 micron yeast cell wall ghost.

Payload Trapping Molecules

The payload trapping molecule is preferably a pharmaceutically acceptable excipient. The payload and trapping molecule are both soluble in the solvent system; the solvent system must be absorbed through the yeast cell particle carbohydrate matrix allowing the absorption of the payload and trapping polymer. The payload and trapping molecule are preferably water soluble. In preferred embodiments, the trapping molecule is biodegradable.

The mechanism of action of the trapping reaction with a given payload dictates the choice of payload trapping molecule. For electrostatic interactions a charged payload trapping molecule of opposite charge of the payload is required. For physical entrapment, the payload trapping molecule suitably participates in the formation of a matrix that reduces the diffusion of a payload. In other embodiments, the payload trapping molecule contributes a hydrophobic binding property that contributes to the retention of the payload. In further embodiments, the payload trapping molecule selectively binds to the payload, providing an affinity interaction that contributes to the retention of the payload.

In general, polyelectrolytes can be suitable payload trapping molecules. Several suitable polyelectrolytes are disclosed in U.S. Pat. No. 6,133,229. The polyelectrolyte may be a cationic or anionic polyelectrolyte. Amphoteric polyelectrolytes may also be employed. The cationic polyelectrolyte is preferably a polymer with cationic groups distributed along the molecular chain. The cationic groups, which in certain embodiments may include quaternary ammonium-derived moieties, may be disposed in side groups pendant from the chain or may be incorporated in it. Examples of cationic polyelectrolytes include: copolymers of vinyl pyrrolidone and quaternary methyl methacrylate e.g., GAFQUAT® series (755N, 734, HS-100) obtained from ISP; substituted polyacrylamides; polyethyleneimine, polypropyleneimine and substituted derivatives; polyamine homopolymers (GOLCHEM® CL118); polyamine co-polymers (e.g., condensates of epichlorohydrin and mono or dimethylamine); polydiallyl dimethyl ammonium chloride (polyDADMAC); substituted dextrans; modified guar gum (substituted with hydroxypropytrimonium chloride); substituted proteins (e.g., quaternary groups substituted on soya protein and hydrolysed collagen); polyamino acids (e.g., polylysine); low molecular weight polyamino compounds (e.g., spermine and spermidine). Natural or artificial polymers may be employed. Cationic polyelectrolytes with MW 150 to 5,000,000, preferably 5000 to 500,000, more preferably 5000 to 100,000 may be employed. An amount of 0.01 to 10% is preferred, more preferably 0.1 to 2% w/v, especially 0.05 to 5%.

The anionic polyelectrolyte is preferably a polymer with anionic groups distributed along the molecular chain. The anionic groups, which may include carboxylate, sulfonate, sulphate or other negatively charged ionisable groupings, may be disposed upon groups pendant from the chain or bonded directly to the polymer backbone. Natural or artificial polymers may be employed.

Examples of anionic polyelectrolytes include: a copolymer of methyl vinyl ether and maleic anhydride, a copolymer of methyl vinyl ether and maleic acid, (Gantrez AN-series and S-series, respectively, International Specialty Products, Wayne, N.J.); alginic acid and salts; carboxymethyl celluloses and salts; substituted polyacrylamides (eg substituted with carboxylic acid groups); polyacrylic acids and salts; polystyrene sulfonic acids and salts; dextran sulphates; substituted saccharides e.g., sucrose octosulfate; heparin. Anionic polyelectrolytes with MW of 150 to 5,000,000 may be used, preferably 5000 to 500,000, more preferably 5000 to 100,000. An amount of 0.01% to 10% is preferred especially 0.05 to 5% more especially 0.1 to 2% w/v.

Biological polymers, such as polysaccharides, are preferred trapping polymers. Preferably, the polymers are processed to an average molecular weight to less than 100,000 Daltons. The polymers are preferably derivatized to provide cationic or anionic characteristics. Suitable polysaccharides include chitosan (deacetylated chitin), alginates, dextrans, such as 2-(diethylamino) ethyl ether dextran (DEAE-dextran) and dextran sulphate, xanthans, locust bean gums and guar gums.

Two general classes of cationic molecules are suitable for use as trapping molecules with negatively charged payloads such as polynucleotides: cationic polymers and cationic lipids.

A wide variety of cationic polymers have been shown to mediate in vitro transfection, ranging from proteins [such as histones (Fritz, J. D., et al, (1996) Hum. Gene Ther. 7, 1395-1404) and high mobility group (HMG) proteins (Mistry A. R., et al. (1997) BioTechniques 22, 718-729)] and polypeptides [such as polylysine (Wu, G. Y. & Wu, C. H. (1987) J. Biol. Chem. 262, 4429-4432, Wagner, E., et al., (1991) Bioconjugate Chem. 2, 226-231, short synthetic peptides (Gottschalk, S., et al., (1996) Gene Ther. 3, 448-457; Wadhwa, M. S., et al., (1997) Bioconjugate Chem. 8, 81-88), and helical amphiphilic peptides (Legendre, J. Y., et al., (1997) Bioconjugate Chem. 8, 57-63; Wyman, T. B., et al., (1997) Biochemistry 36, 3008-3017)] to synthetic polymers [such as polyethyleneimine (Boussif, O., et al., (1996) Gene Ther. 3, 1074-1080), cationic dendrimers (Tang, M. X., et al., (1996) Bioconjugate Chem. 7, 703-714; Haensler, J. et al., (1993) Bioconjugate Chem. 4, 372-379), and glucaramide polymers (Goldman, C. K., et al., (1997) Nat. Biotech. 15, 462-466)]. Other suitable cationic polymers include N-substituted glycine oligomers (peptoids) (Murphy, J. E., et al, A combinatorial approach to the discovery of efficient cationic peptoid reagents for gene delivery, Proc Natl Acad. Sci. USA, 1998 95 (4)1517-1522), poly(2-methyl-acrylic acid 2-[(2-dimethylamino)-ethyl)-methylamino]-ethyl ester), abbreviated as pDAMA, and poly(2-dimethylamino ethyl)-methacrylate (pDMAEMA) (Funhoff, A. M., et al., 2004 Biomacromolecules, 5, 32-39).

Cationic lipids are also known in the art to be suitable for transfection. Felgner, P.L1, et al., Lipofection: a highly efficient, lipid-mediated DNA-transfection procedure. Proc Natl Acad Sci USA. 1987 84(21):7413-7. Suitable cationic lipids include N-[1-(2,3-dioleyloxy)propyl]-N,N,N-trimethylammonium chloride (DOTMA), [N,N,N',N'-tetramethyl-N,N'-bis(2-hydroxyethyl)-2,3-di(oleoyloxy)-1,4-butanediammonium iodide](Promega Madison, Wis., USA), dioctadecylamidoglycyl spermine (Promega Madison, Wis., USA), N-[1-(2,3-Dioleoyloxy)]-N,N,N-trimethylammonium propane methylsulfate (DOTAP), N-[1-(2,3-dioleyloxy)propyl]-N,N,N-trimethylammonium chloride, 1,2-dimyristyloxypropyl-3-dimethyl-hydroxy ethyl ammonium bromide (DMRIE), dimyristoleoyl phosphonomethyl trimethyl ammonium (DMPTA) (see Floch et al. 1997. Cationic phosphonolipids as non-viral vectors for DNA transfection in hematopoietic cell lines and CD34+ cells. Blood Cells, Molec. & Diseases 23: 69-87), 1,2-dioleoyl-sn-glycero-3-phosphoethanolamine-N-(7-nitro-2-1,3-benzoxadiazol-4-yl), ammonium salt (Avanti Polar Lipids, Inc. Alabaster, Ala., US), 1,2-dioleoyl-3-trimethylammonium-propane chloride (Avanti Polar Lipids, Inc. Alabaster, Ala., US), 1,2-dioleoyl-sn-glycero-3-phosphoethanolamine (Avanti Polar Lipids, Inc. Alabaster, Ala., US) and 1,3-dioleoyloxy-2-(6-carboxyspermyl)propylamide (DOSPER).

Polyamines suitable as cationic trapping molecules are described in U.S. Pat. Nos. 6,379,965 and 6,372,499.

Payload Molecules

The particulate delivery system of the present invention is useful for in vivo or in vitro delivery of payload molecules including, but limited to, polynucleotides such as oligonucleotides, antisense constructs, siRNA, enzymatic RNA, and recombinant DNA constructs, including expression vectors.

In other preferred embodiments, the particulate delivery system of the present invention is useful for in vivo or in vitro delivery of payload molecules such as amino acids, peptides and proteins. By "protein" is meant a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, preferably at least about 20 kD.

Examples of proteins encompassed within the definition herein include mammalian proteins, such as, e.g., growth hormone (GH), including human growth hormone, bovine growth hormone, and other members of the GH supergene family; growth hormone releasing factor, parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; alpha tumor necrosis factor, beta tumor necrosis factor; enkephalinase; RANTES (regulated on activation normally T-cell expressed and secreted); human macrophage inflammatory protein (MIP-1-alpha); serum albumin such as human serum albumin; mullerian-inhibiting substance; relaxin A-chain; relaxin B-chain; prorelaxin; mouse gonadotropin-associated peptide; DNase; inhibin; activin; vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-beta; platelet-derived growth factor (PDGF); fibroblast growth factor such as aFGF and bFGF; epidermal growth factor (EGF); transforming growth factor (TGF) such as TGF-alpha and TGF-beta, including TGF-beta1, TGF-beta2, TGF-beta3, TGF-beta4, or TGF-beta5; insulin-like growth factor-I and -II (IGF-I and IGF-II); des(1-3)-IGF-I (brain IGF-I); insulin-like growth factor binding proteins; CD proteins such as CD3, CD4, CD8, CD19 and CD20; osteoinductive factors; immunotoxins; a bone morphogenetic protein (BMP); T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides.

The members of the OH supergene family include growth hormone, prolactin, placental lactogen, erythropoietin, thrombopoietin, interleukin-2, interleukin-3, interleukin-4, interleukin-5, interleukin-6, interleukin-7, interleukin-9, interleukin-10, interleukin-11, interleukin-12 (p35 subunit), interleukin-13, interleukin-15, oncostatin M, ciliary neurotrophic factor, leukemia inhibitory factor, alpha interferon, beta interferon, gamma interferon, omega interferon, tau interferon, granulocyte-colony stimulating factor, granulocyte-macrophage colony stimulating factor, macrophage colony stimulating factor, cardiotrophin-1 and other proteins identified and classified as members of the family.

The protein payload molecule is preferably essentially pure and desirably essentially homogeneous (i.e. free from contaminating proteins etc). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition. Proteins may be derived from naturally occurring sources or produced by recombinant technology. Proteins include protein variants produced by amino acid substitutions or by directed protein evolution (Kurtzman, A. L., et al., Advances in directed protein evolution by recursive genetic recombination: applications to therapeutic proteins, Curr Opin Biotechnol. 2001 12(4): 361-70) as well as derivatives, such as PEGylated proteins.

In certain embodiments, the protein is an antibody. The antibody may bind to any of the above-mentioned molecules, for example. Exemplary molecular targets for antibodies encompassed by the present invention include CD proteins such as CD3, CD4, CD8, CD19, CD20 and CD34; members of the HER receptor family such as the EGF receptor, HER2, HER3 or HER4 receptor; cell adhesion molecules such as LFA-1, Mol, p150,95, VLA-4, ICAM-1, VCAM and alphav/beta3 integrin including either alpha or beta subunits thereof (e.g. anti-CD11a, anti-CD18 or anti-CD11b antibodies); growth factors such as VEGF; IgE; blood group antigens; flk2/flt3 receptor; obesity (OB) receptor; protein C, etc.

In addition to peptides, polypeptides and polynucleotides, the particulate delivery system of the present invention is suitable for the delivery of smaller molecules, preferably for the delivery of pharmaceutically active agent, more preferably therapeutic small molecules. Suitable small molecule payloads for the delivery system of the present invention include contraceptive agents such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimethisterone, megestrol acetate, chlormadinone acetate, norgestimate, norethisterone, ethisterone, melengestrol, norethynodrel and the like; and spermicidal compounds such as nonylphenoxypolyoxyethylene glycol, benzethonium chloride, chlorindanol and the like. Preferably, for such steroidal payloads, a mixture of trapping molecules is used, comprising a sufficient amount of a detergent to solubilize the payload and a polymer to retain the payload within the yeast cell wall particle.

Other active agents that can be incorporated in the delivery system of the present invention include gastrointestinal therapeutic agents such as aluminum hydroxide, calcium carbonate, magnesium carbonate, sodium carbonate and the like; non-steroidal antifertility agents; parasympathomimetic agents; psychotherapeutic agents; major tranquilizers such as chloropromazine HCl, clozapine, mesoridazine, metiapine, reserpine, thioridazine and the like; minor tranquilizers such as chlordiazepoxide, diazepam, meprobamate, temazepam and the like; rhinological decongestants; sedative-hypnotics such as codeine, phenobarbital, sodium pentobarbital, sodium secobarbital and the like; other steroids such as testosterone and testosterone propionate; sulfonamides; sympathomimetic agents; vaccines; vitamins and nutrients such as the essential amino acids, essential fats and the like; antimalarials such as 4-aminoquinolines, 8-aminoquinolines, pyrimethamine and the like; anti-migraine agents such as mazindol, phentermine and the like; anti-Parkinson agents such as L-dopa; anti-spasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocomine methanesulfonate, dihydroergokroyptine methanesulfate and combinations thereof; alkaloids such as atropine sulfate, Belladonna, hyoscine hydrobromide and the like; analgesics; narcotics such as codeine, dihydrocodienone, meperidine, morphine and the like; non-narcotics such as salicylates, aspirin, acetaminophen, d-propoxyphene and the like.

In preferred embodiments, the system of the present invention is used to deliver antibiotics such as the cephalosporins, chloramphenical, gentamicin, kanamycin A, kanamycin B, the penicillins, ampicillin, streptomycin A, antimycin A, chloropamtheniol, metronidazole, oxytetracycline penicillin G, the tetracyclines, and the like. In preferred embodiments, the ability of the body's macrophages to inactivate pathogens is enhanced by the delivery of antibiotics, such as tetracycline, to the macrophages.

In other preferred embodiments, the present invention provides a system to deliver anti-cancer agents; anti-convulsants such as mephenyloin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa, chlorambucil, cyclophosphamide, melphalan, nitrogen mustard, methotrexate and the like.

Vaccines

In preferred embodiments, the particulate delivery system of the present invention is useful in providing oral delivery of vaccines. In preferred embodiments, the system is used to deliver antigens, such as antigens of such microorganisms as *Neisseria gonorrhea, Mycobacterium tuberculosis,* Herpes virus (*humonis,* types 1 and 2), *Candida albicans, Candida tropicalis, Trichomonas vaginalis, Haemophilus vaginalis,* Group B *Streptococcus* sp., *Microplasma hominis, Hemophtlus ducreyi, Granuloma inguinale, Lymphopathia venereum, Treponema pallidum, Brucella abortus, Brucella melitensis, Brucella suis, Brucella cents, Campylobacter fetus, Campylobacrer fetus intestinalis, Leptospira pomona, Listeria monocytogenes, Brucella ovis,* equine herpes virus 1, equine arteritis virus, IBR-IBP virus, BVD-MB virus, *Chlamydia psittaci, Trichomonas foetus, Toxoplasma gondii, Escherichia coli, Actinobacillus equuli, Salmonella aborrus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum* and the like. In other embodiments, the system can be used to deliver neutralizing antibodies that counteract the above microorganisms.

In other embodiments, the system can be used to deliver enzymes such as ribonuclease, neuramidinase, trypsin, glycogen phosphorylase, sperm lactic dehydrogenase, sperm hyaluronidase, adenossinetriphosphatase, alkaline phosphatase, alkaline phosphatase esterase, amino peptidase, trypsin chymotrypsin, amylase, muramidase, acrosomal proteinase, diesterase, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, DPN-di-aprorase.

In preferred embodiments, the system can deliver antigens of bioterrorism critical biological agents, including Category A agents such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; and Category C agents such as nipah virus, hantaviruses, tickborne hemorrhagic fever viruses, tickborne encephalitis viruses, yellow fever, and multidrug-resistant tuberculosis.

In preferred embodiments, the system can be used to deliver inactivated antigenic toxins, such as anatoxin antigens, including toxoids (inactivated but antigenic toxins), and toxoid conjugates. In preferred embodiments, the toxoid is an inactivated microbial toxin. In other embodiments, the toxoid is an inactivated plant toxin. In further embodiments, the toxoid is an inactivated animal toxin. In certain embodiments, the system can be used to deliver toxoids such as pertussis toxoid, *Corynebacterium diphtheriae* toxoid, tetanus toxoid, *Haemophilus influenzae* type b-tetanus toxoid conjugate, *Clostridium botulinum* D toxoid, *Clostridium borulinum* E toxoid, toxoid produced from Toxin A of *Clostridium difficile, Vibrio cholerae* toxoid, *Clostridium perfringens* Types C and D toxoid, *Clostridium chauvoei* toxoid, *Clostridium novyi* (Type B) toxoid, *Clostridium septicum* toxoid, recombinant HIV tat IIIB toxoid, *Staphylococcus* toxoid, *Actinobacillus pleuropneumoniae* Apx I toxoid, *Actinobacillus pleuropneumoniae* Apx II toxoid, *Actinobacillus pleuropneumoniae* Apx III toxoid, *Actinobacillus pleuropneumoniae* outer membrane protein (OMP) toxoid, *Pseudomonas aeruginosa* elastase toxoid, snake venom toxoid, ricin toxoid, *Mannheimia haemolytica* toxoid, *Pasteurella multocida* toxoid, *Salmonella typhimurium* toxoid, *Pasteurella multocida* toxoid, and *Bordetella bronchiseptica* toxoid.

Techniques of making a toxoid from a corresponding toxin, e.g. chemical treatment with formaldehyde or aluminum salts or gamma irradiation, are known in the art. Recombinant methods of converting a toxin to a toxoid are also known (Fromen-Romano, C., et al., Transformation of a non-enzymatic toxin into a toxoid by genetic engineering, Protein Engineering vol. 10 no. 10 pp. 1213-1220, 1997). In preferred embodiments, the system of the present invention can be used to deliver a recombinant toxoid. In other preferred embodiments, the system of the present invention can be used to deliver an expression vector encoding a recombinant toxoid.

In order to produce a genetic vaccine to protect against pathogen infection, genetic material which encodes immunogenic proteins against which a protective immune response can be mounted, must be included in the nucleic acid composition. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The nucleic acid composition used in the genetic vaccine can include genetic material that encodes many pathogen antigens. For example, several viral genes may be included in a single construct, thereby providing multiple targets. In addition, multiple inoculants which can be delivered to different cells in an individual can be prepared to collectively include, in some cases, a complete or, more preferably, an incomplete, e.g., nearly complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

In accordance with the present invention there is also provided a method of conferring a broad based protective immune response against hyperproliferating cells that are characteristic of hyperproliferative diseases, as well as a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a nucleic acid composition that includes a nucleotide sequence which encodes an immunogenic "hyperproliferating cell"-associated protein into the cells of an individual, results in the production of those proteins in the vaccinated cells of an individual. As used herein, the term "hyperproliferative-associated protein" is meant to refer to proteins that are associated with a hyperproliferative disease. To immunize against hyperproliferative diseases, a nucleic acid composition that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation genes bcr/abl, ras, src, P53, neu, trk and EGRF. In addition to oncogene products as target antigens, target proteins for anti-cancer treatments and protective regimens include variable regions of antibodies made by B cell lymphomas, and variable regions of T cell receptors of T cell lymphomas which, in some embodiments, are also used as target antigens for autoimmune diseases. Other tumor-associated proteins can be used as target proteins, such as proteins which are found at higher levels in tumor cells, including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and biotechnology, as well as epidemiology, allow for the determination of probability and risk assessment for the development of cancer in an individual. Using genetic screening and/or family health histories, it is possible to predict the probability that a particular individual has for developing any one of several types of cancer.

Similarly, those individuals who have already developed cancer and who have been treated to remove the cancer, or are otherwise in remission, are particularly susceptible to relapse and reoccurrence. As part of a treatment regimen, such individuals can be immunized against the cancer that they have been diagnosed as having had in order to combat such a recurrence. Thus, once it is known that individuals have had a type of cancer and are at risk of a relapse, they can be immunized in order to prepare their immune systems to combat any future appearance of the cancer.

The present invention also provides a method of treating individuals suffering from hyperproliferative diseases. In such methods, the introduction of peptide, protein, carbohydrate or nucleic acid compositions and combinations thereof serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity, including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a composition composed of peptide, protein, carbohydrate or nucleic acid compositions and combinations thereof that delivers or encodes at least one of these proteins will elicit an immune response that will target T cells involved in RA. See: Howell, M. D., et al., 1991 Proc. Natl. Acad. Sci. USA 88:10921-10925; Paliard, X., et al., 1991 Science 253:325-329; Williams, W. V., et al., 1992 J. Clin. Invest. 90:326-333; each of which is incorporated herein by reference.

In MS, several specific variable regions of TCRs which are involved in the disease have been characterized. These TCRs include Vβ-7 and Vα-10. Thus, vaccination with a composition composed of peptide, protein, carbohydrate or nucleic acid compositions and combinations thereof that delivers or encodes at least one of these proteins will elicit an immune response that will target T cells involved in MS. See: Wucherpfennig, K. W., et al., 1990 Science 248:1016-1019; Oksenberg, J. R., et al., 1990 Nature 345:344-346; each of which is incorporated herein by reference.

In scleroderma, several specific variable regions of TCRs which are involved in the disease have been characterized. These TCRs include V-β-6, Vβ-8, Vβ-14 and Vα-16, Vα-3C, Vα-7, Vα-14, Vα-15, Vα-16, Vα-28 and Vα-12. Thus, vaccination with a composition composed of peptide, protein, carbohydrate or nucleic acid compositions and combinations thereof that delivers or encodes for at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of such antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Vaccines can be prepared using this information.

In the case of SLE, one antigen is believed to be DNA. Thus, in patients to be immunized against SLE, their sera can be screened for anti-DNA antibodies and a vaccine can be prepared which includes nucleic acid compositions that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 Sequence of Proteins of Immunological Interest U.S. Department of Health and Human Services, Bethesda Md., which is incorporated herein by reference. In addition, a general method for cloning functional variable regions from antibodies can be found in Chaudhary, V. K., et al., 1990 Proc. Natl. Acad. Sci. USA 87:1066, which is incorporated herein by reference.

Gene Therapy

In preferred embodiments, the present invention provides compositions and methods for the treatment of genetic disorders or conditions having a genetic component. In further preferred embodiments, the present invention provides compositions useful for the manufacture of pharmaceutical products for the treatment of genetic disorders or conditions having a genetic component.

The Human Genome Project has increased our knowledge of the genetic basis of disease. See, generally, http://www.ornl.gov/sci/techresources/Human_Genome/medicine/assist.shtml.

Both environmental and genetic factors have roles in the development of any disease. A genetic disorder is a disease caused by abnormalities in an individual's genetic material (genome). There are four different types of genetic disorders: (1) single-gene, (2) multifactorial, (3) chromosomal, and (4) mitochondrial.

(1) Single-gene (also called Mendelian or monogenic)—This type is caused by changes or mutations that occur in the DNA sequence of one gene. Genes code for proteins, the molecules that carry out most of the work, perform most life functions, and even make up the majority of cellular structures. When a gene is mutated so that its protein product can no longer carry out its normal function, a disorder can result. There are more than 6,000 known single-gene disorders, which occur in about 1 out of every 200 births. Some examples are cystic fibrosis, sickle cell anemia, Marfan syndrome, Huntington's disease, and hereditary hemochromatosis.

(2) Multifactorial (also called complex or polygenic)—This type is caused by a combination of environmental factors and mutations in multiple genes. For example, different genes that influence breast cancer susceptibility have been found on chromosomes 6, 11, 13, 14, 15, 17, and 22. Its more complicated nature makes it much more difficult to analyze than single-gene or chromosomal disorders. Some of the most common chronic disorders are multifactorial disorders. Examples include heart disease, high blood pressure, Alzheimer's disease, arthritis, diabetes, cancer, and obesity. Multifactorial inheritance also is associated with heritable traits such as fingerprint patterns, height, eye color, and skin color.

(3) Chromosomal—Chromosomes, distinct structures made up of DNA and protein, are located in the nucleus of each cell. Because chromosomes are carriers of genetic material, such abnormalities in chromosome structure as missing or extra copies or gross breaks and rejoinings (translocations), can result in disease. Some types of major chromosomal abnormalities can be detected by microscopic examination. Down syndrome or trisomy 21 is a common disorder that occurs when a person has three copies of chromosome 21.

(4) Mitochondrial—This relatively rare type of genetic disorder is caused by mutations in the nonchromosomal DNA of mitochondria. Mitochondria are small round or rod-like organelles that are involved in cellular respiration and found in the cytoplasm of plant and animal cells. Each mitochondrion may contain 5 to 10 circular pieces of DNA.

In preferred embodiments, the particulate delivery system of the present invention is used to administer at least one polynucleotide comprising a compensating gene. In other preferred embodiments, the particulate delivery system of the present invention is used to administer at least one polynucleotide encoding a gene product of a missing gene, wherein the expression of the gene product is useful in the treatment of the genetic disorder or the genetic component of a condition. In preferred embodiments, the particulate delivery system of the present invention including the desired payload molecule is useful for the manufacture of a pharmaceutical product for the treatment of genetic disorder or the genetic component of a condition. Such pharmaceutical products are suitably administered orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. The pharmaceutical products are preferably administered orally, buccally, and parenterally, more preferably orally. Particles loaded with different payloads, e.g. a polynucleotide, a polynucleotide expression vector or a small molecule therapeutic can be mixed in the appropriate proportions and administered together, e.g., in a capsule, for combination therapy.

In aspects of the present invention that relate to gene therapy, the nucleic acid compositions contain either compensating genes or genes that encode therapeutic proteins. Examples of compensating genes include a gene that encodes dystrophin or a functional fragment, a gene to compensate for the defective gene in patients suffering from cystic fibrosis, a gene to compensate for the defective gene in patients suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, nucleic acid compositions which encode single chain antibody components which specifically bind to toxic substances can be administered. In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is wheelchair-bound by age 13 and usually dies by age 20. In some patients, particularly those suffering from BMD, partial dystrophin protein produced by expression of a mini-gene delivered according to the present invention can provide improved muscle function.

In preferred embodiments, the particulate delivery system of the present invention provides compositions and methods for the treatment of genetic disorders and conditions believed to have a genetic component, such as Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry Syndrome, colon cancer, congenital adrenal hyperplasia (CAH), Cornelia de Lange Syndrome, Costello Syndrome, Cowden Syndrome, Craniofrontonasal Dysplasia, Crigler-Najjar Syndrome, Creutzfeldt-Jakob Disease (CJD), cystic fibrosis, deafness, depression, diabetes, diastrophic dysplasia, DiGeorge Syndrome, Down's Syndrome, dyslexia, Duchenne muscular dystrophy, Dubowitz syndrome, ectodermal dysplasia, Ellis-van Creveld syndrome, Ehlers-Danlos, Epidermolysis Bullosa (EB), epilepsy, essential tremor, familial hypercholesterolemia, familial Mediterranean fever, Fragile X Syndrome, Friedreich's ataxia, Gaucher disease, glaucoma, glucose galactose malabsorption, glutaricaciduria, gyrate atrophy, Goldberg Shprintzen Syndrome (velocardiofacial syndrome), Gorlin Syndrome, Hailey-Hailey Disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's Syndrome, Kabuki Syndrome, Leigh's Disease (or Syndrome) Long QT Syndrome, lung cancer, malignant melanoma, manic depression, Marfan Syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan Syndrome, obesity, ovarian cancer, p53 tumor suppressor, pancreatic cancer, Parkinson disease, paroxysmal nocturnal hemoglobinuria, Pendred syndrome, peroneal muscular atrophy, phenylketonuria (PKU), polycystic kidney disease, Prader-Willi Syndrome, primary biliary cirrhosis, prostate cancer, REAR Syndrome, Refsum disease, retinitis pigmentosa, retinoblastoma, Rett Syndrome, Sanfilippo Syndrome, schizophrenia, severe combined immunodeficiency, sickle cell anemia, spina bifida, spinal muscular atrophy, spinocerebellar atrophy, SRY: sex determination, Sudden Adult Death Syndrome, Tangier disease, Tay-Sachs disease, thrombocytopenia absent radius syndrome, Townes-Brocks Syndrome, tuberous sclerosis, Turner syndrome, Usher syndrome, von Hippel-Lindau syndrome, Waardenburg syndrome, Weaver syndrome, Werner syndrome, Williams syndrome, Wilson's Disease, xeroderma pigmentosum and Zellweger syndrome.

In other preferred embodiments, the particulate delivery system of the present invention provides compositions and methods for the treatment of genetic disorders and conditions believed to have a genetic component that are manifested as metabolic disorders, such as protein-related disorders, including Sickle-Cell Anemia and beta-Thalassemias, alpha-Thalassemias, Marfan's Syndrome, Ehlers-Danlos Type I, Ehlers-Danlos Type II, Ehlers-Danlos Type m, Ehlers-Danlos Type IV autosomal dominant, Ehlers-Danlos Type IV autosomal recessive, Ehlers-Danlos Type IV-D, Ehlers-Danlos Type V, Ehlers-Danlos Type VI, Ehlers-Danlos Type VII autosomal dominant, Ehlers-Danlos Type VII autosomal recessive, Ehlers-Danlos Type VIII. Ehlers-Danlos with Platelet Dysfunction, Cutis Laxa, Cutis Laxa recessive Type I, Occipital Horn Syndrome Cutis Laxa, X-linked, Osteogenesis Imperfecta Type I, Osteogenesis Imperfecta Type I-C, Osteogenesis Imperfecta Silent Type II/II, Osteogenesis Imperfecta Type IV, Osteogenesis Imperfecta Neonatal Lethal form, and Osteogenesis Imperfecta progressively deforming.

In further preferred embodiments, the particulate delivery system of the present invention provides compositions and methods for the treatment of genetic disorders of the clotting system, such as afibrinogenemia, complete loss of fibrinogen, Factor I; dysfibrinogenemia dysfunctional fibrinogen, Factor I; Factor II disorders; tissue factor deficiency; Factor V deficiency, labile Factor deficiency, Factor VII deficiency, Factor VIII deficiency (Hemophilia A), Factor IX deficiency (Hemophilia B), Factor X deficiency, Factor XI deficiency, Rosenthal Syndrome, Plasma Thromboplastin Antecedent (PTA) deficiency, Factor XII deficiency, Hageman factor deficiency, Factor XIII deficiency, Factor V & VIII Combined deficiency, Factor VIII & IX combined deficiency, Factor IX & XI Combined deficiency, Protein C deficiency, Protein S deficiency, thrombophilia, antithrombin III deficiency, giant platelet syndrome, platelet glycoprotein Ib deficiency, von Willebrand disease, Fletcher Factor deficiency and prekallikrein deficiency.

In further preferred embodiments, the particulate delivery system of the present invention provides compositions and methods for the treatment of glycogen storage disorders, such as Type 0, Type I (von Gierke's disease), Type Ib, Type Ic, Type II (Pompe disease), Type IIb (Danon disease), Type III (Cori disease or Forbes disease), Type IV (Andersen disease), Type V (McArdle disease), Type VI (Hers disease), Type VII (Tarui disease), Type VIII, Type IX, and Type XI (Fanconi-Bickel syndrome).

In yet further preferred embodiments, the particulate delivery system of the present invention provides compositions and methods for the treatment of defects in fructose, galactose and glycerol metabolism, such as hereditary fructose intolerance, aldolase B deficiency; fructosuria, hepatic fructokinase deficiency; classic galactosemia, galactose epimerase deficiency; galactokinase deficiency; hyperglycerolemia and glycerol kinase deficiency.

In yet further preferred embodiments, the particulate delivery system of the present invention provides compositions and methods for the treatment of defects in cholesterol and lipoprotein metabolism, such as apolipoprotein(a)—Lp(a), hyperlipoproteinemia Type I; hyperlipoproteinemia Type Ib; apolipoprotein C-II deficiency; hyperlipoproteinemia Type Ic, chylomicronemia; familial hypercholesterolemia, Type II hyperlipoproteinemia; hyperlipoproteinemia Type II, familial hyperbetalipoproteinemia; hyperlipoproteinemia Type III, apolipoprotein E deficiency; hyperlipoproteinemia Type IV; hyperlipoproteinemia Type V; familial LCAT deficiency; Wolman disease; lipoprotein lipase deficiency; familial hypertriglyceridemia; hyperlipidemia Type V; hyperlipidemia Type VI; familial ligand-defective apo-B; familial hyperalphalipoproteinemia; hypobetalipoproteinemia, apolipoprotein B-100 deficiency; abetalipoproteinemia, Kornzweig syndrome; and Tangier Disease, familial high-density lipoprotein deficiency.

In yet further preferred embodiments, the particulate delivery system of the present invention provides compositions and methods for the treatment of mucopolysaccharide and glycolipid disorders, such as Type I H mucopolysaccharidosis (Hurler syndrome), Type I S mucopolysaccharidosis (Scheie syndrome), Type I H/S mucopolysaccharidosis (Hurler/Scheie syndrome), Type II mucopolysaccharidosis (Hunter's syndrome), Type III mucopolysaccharidoses (Sanfilippo Type A, Sanfilippo Type B, Sanfilippo Type C, Sanfilippo Type D), Type IV mucopolysaccharidosis (Morquio's Type A, Morquio's Type B), Type VI mucopolysaccharidosis (Maroteaux-Lamy Syndrome) and Type VII mucopolysaccharidosis (Sly Syndrome).

In other preferred embodiments, the particulate delivery system of the present invention provides compositions and methods for the treatment of disorders of glycosphingolipid metabolism, such as GM1 gangliosidoses, including generalized GM1 Type II, juvenile form; generalized GM1 Type III, adult form; GM2 gangliosidosis, Sandhoff-Jatzkewitz disease; GM3 gangliosidoses, Tay-Sachs disease, Tay-Sachs AB variant, Gaucher disease, Niemann-Pick Disease, Types A, B, C1, C2 and D, Schindler disease, Fabry disease, lactosylceramidosis, Farber disease, Krabbe disease, multiple sulfatase deficiency, Austin disease, metachromic leukodystrophy, and sulfatide lipodosis.

In other preferred embodiments, the particulate delivery system of the present invention provides compositions and methods for the treatment of oligosaccharidoses such as fucosidosis, mucolipodosis VI, sialolipidosis, alpha-mannosidosis, beta-mannosidosis, sialidoses Types I and II, galactosialidosis, Goldberg syndrome and aspartylglucosaminuria.

In other preferred embodiments, the particulate delivery system of the present invention provides compositions and methods for the treatment of disorders of lysosomal enzyme transport such as mucolipidosis I, sialidosis; mucolipodosis II, I-cell disease; and mucolipodosis III, pseudo-Hurler polydystrophy.

In other preferred embodiments, the particulate delivery system of the present invention provides compositions and methods for the treatment of defects in amino acid and organic acid metabolism such as phenylketonuria; Type I tyrosinemia, tyrosinosis; Type II tyrosinemia, Richner-Hanhart syndrome; Type III tyrosinemia; alcaptonuria; homocystinuria; histidinemia; maple syrup urine disease (MSUD); MSUD Type Ib, MSUD type II; methylmalonic aciduria; non-ketonic hyperglycinemia Type I (NKHI) and hyperlysinemia.

In other preferred embodiments, the particulate delivery system of the present invention provides compositions and methods for the treatment of urea cycle defects such as hyperammonemias; carbamoyl phosphate synthetase I (CPS-I) deficiency; ornithine transcarbamylase (OTC) deficiency; N-acetylglutamate synthetase deficiency; argininosuccinic aciduria, argininosuccinate lyase deficiency; hyperargininemia, arginase deficiency; citrullinemia, argininosuccinate synthetase deficiency and ornithine aminotransferase deficiency. In other preferred embodiments, the particulate delivery system of the present invention provides compositions and methods for the treatment of defects in amino acid transport such as cystinuria Type I; cystinuria Type III; Hartnup disease and hyperammonemia-hyperornithinemia-homocitrullinuria (HHH) syndrome. In other preferred embodiments, the particulate delivery system of the present invention provides compositions and methods for the treatment of porphyrias and bilirubinemias such as congenital erythropoietic porphyria (CEP); erythropoietic protoporphyria (EPP); ALA dehydratase deficiency porphyria (ADP); acute intermittent porphyria (AIP); hereditary coproporphyria (HCP); variegate porphyria (VP); porphyria cutanea tarda (PCT); hepatoerythropoietic porphyria (HEP); Gilbert Syndrome; Crigler-Najjar Syndrome, Types I and I; Dubin-Johnson syndrome and Rotor syndrome.

In other preferred embodiments, the particulate delivery system of the present invention provides compositions and methods for the treatment of errors in fatty acid metabolism such as very-long-chain acyl-CoA dehydrogenase deficiency (VLCAD); long-chain acyl-CoA dehydrogenase deficiency (LCAD); medium-chain acyl-CoA dehydrogenase deficiency (MCAD); short-chain acyl-CoA dehydrogenase deficiency (SCAD; carnitine translocase deficiency; carnitine palmitoyltransferase I (CPT I) deficiency and carnitine palmitoylransferase II (CPT II) deficiency. In other preferred embodiments, the particulate delivery system of the present invention provides compositions and methods for the treatment of defects in nucleotide metabolism such as Lesch-Nyhan syndrome; Severe Combined Immunodeficiency Disease (SCID), due to adenosine deaminase (ADA) deficiency; gout; renal lithiasis, due to adenine phosphoribosyltransferase (APRT) deficiency; xanthinuria, due to xanthine oxidase deficiency; orotic aciduria, Types I & I and ornithine transcarbamoylase deficiency.

In other preferred embodiments, the particulate delivery system of the present invention provides compositions and methods for the treatment of disorders in metal metabolism and transport such as Wilson disease, Menkes disease, occipital horn syndrome and hemochromatosis. In other preferred embodiments, the particulate delivery system of the present invention provides compositions and methods for the treatment of disorders in peroxisomes such as Zellweger syndrome, X-linked adreoleukodystrophy, neonatal adrenoleukodystophy (NALD), rhizomelic chondrodysplasia punctata (RCDP) and infantile Refsum's disease (IRD). In other preferred embodiments, the particulate delivery system of the present invention provides compositions and methods for the treatment of disorders associated with defective DNA repair such as ataxia telangiectasia (AT), xeroderma pigmentosum (XP), Cockayne syndrome, Bloom syndrome and Fanconi anemia.

Routes of Administration

Routes of administration include but are not limited to oral; buccal, sublingual, pulmonary, transdermal, transmucosal, as well as subcutaneous, intraperitoneal, intravenous, and intramuscular injection. Preferred routes of administration are oral; buccal, sublingual, pulmonary and transmucosal.

The particulate delivery system of the present invention is administered to a patient in a therapeutically effective amount. The particulate delivery system can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using a controlled release formulation. It is also noted that the dose of the compound can be varied over time. The particulate delivery system can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about 2 grams of the active ingredient, and preferably comprises from about 200 milligrams to about 1.0 gram of the active ingredient.

In addition, a particulate delivery system of the present invention can be administered alone, in combination with a particulate delivery system with a different payload, or with other pharmaceutically active compounds. The other pharmaceutically active compounds can be selected to treat the same condition as the particulate delivery system or a different condition.

If the patient is to receive or is receiving multiple pharmaceutically active compounds, the compounds can be administered simultaneously or sequentially in any order. For example, in the case of tablets, the active compounds may be found in one tablet or in separate tablets, which can be administered at once or sequentially in any order. In addition, it should be recognized that the compositions can be different forms. For example, one or more compounds may be delivered via a tablet, while another is administered via injection or orally as a syrup.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein.

For example, a kit may comprise two separate pharmaceutical compositions comprising respectively a first composition comprising a particulate delivery system and a pharmaceutically acceptable carrier; and composition comprising second pharmaceutically active compound and a pharmaceutically acceptable carrier. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and a sheet of relatively stiff material is sealed against the plastic foil at the face of the foil which is opposite from the direction in which the recesses were formed. As a result, the tablets or capsules are sealed in the recesses between the plastic foil add the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day. Also, a daily dose of a particulate delivery system composition can consist of one tablet or capsule, while a daily dose of the second compound can consist of several tablets or capsules and vice versa. The memory aid should reflect this and assist in correct administration.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered micro-chip memory coupled with a liquid crystal readout, or audible reminder signal which, for example, reads out the date that the last daily dose has been taken and/or reminds one when the next dose is to be taken.

A particulate delivery system composition, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions, Examples of suitable aqueous and nonaqueous carriers, diluents, solvents, or vehicles include water, isotonic saline, ethanol, polyols (propylene glycol, polyethylene glycol glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation can comprise pharmaceutically acceptable polymeric or hydrophobic materials such as an emulsion, an ion exchange resin, a sparingly soluble polymer, or a sparingly soluble salt.

These compositions may also contain adjuvants such as preserving, wetting, emulsifying, and/or dispersing agents. Prevention of microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an aliquot of the particulate delivery system and a biodegradable polymer. In preferred embodiments, a suitable biodegradable polymer can be selected from the group consisting of a polyaspartate, polyglutamate, poly(L-lactide), a poly (D,L-lactide), a poly(lactide-co-glycolide), a poly(ε-caprolactone), a polyanhydride, a poly(beta-hydroxy butyrate), a poly(ortho ester) and a polyphosphazene.

Solid dosage forms for oral administration include capsules, tablets, powders, and granules. In such solid dosage forms, the particulate delivery system is optionally admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the particulate delivery system can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the particulate delivery system, e.g. in the region of the Peyer's patches in the small intestine. By way of example, a material such as glyceryl monostearate or glyceryl distearate can be used to coat tablets. Further by way of example, tablets can be coated using methods described in U.S. Pat. Nos. 4,256,108; 4,160, 452; and 4,265,874 to form osmotically-controlled release tablets, Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the particulate delivery system in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the particulate delivery system can be made using a physiologically degradable composition, such as gelatin. Such hard capsules comprise the particulate delivery system, and can further comprise additional ingredients including, for example, an inert solid diluent such as calcium carbonate, calcium phosphate, or kaolin. Soft gelatin capsules comprising the particulate delivery system can be made using a physiologically degradable composition, such as gelatin. Such soft capsules comprise the particulate delivery system, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the particulate delivery system to a specific location within the gastrointestinal tract. Such systems permit delivery at a predetermined time and can be used to deliver the particulate delivery system, optionally together with other additives that my alter the local microenvironment to promote stability and uptake, directly without relying on external conditions other than the presence of water to provide in vive release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like. Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrdidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

In other embodiments, the pharmaceutical composition can be prepared as a nutraceutical, i.e., in the form of, or added to, a food (e.g., a processed item intended for direct consumption) or a foodstuff (e.g., an edible ingredient intended for incorporation into a food prior to ingestion). Examples of suitable foods include candies such as lollipops, baked goods such as crackers, breads, cookies, and snack cakes, whole, pureed, or mashed fruits and vegetables, beverages, and processed meat products. Examples of suitable foodstuffs include milled grains and sugars, spices and other seasonings, and syrups. The particulate delivery systems described herein are preferably not exposed to high cooking temperatures for extended periods of time, in order to minimize degradation of the compounds.

Compositions for rectal or vaginal administration can be prepared by mixing a particulate delivery system with suitable non-irritating excipients or carriers such as cocoa butter, polyethylene glycol or a suppository wax, which are solid at ordinary room temperature, but liquid at body temperature, and therefore, melt in the rectum or vaginal cavity and release the particulate delivery system. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for pulmonary administration via the buccal cavity. Such compositions are conveniently in the form of dry powders for administration using a device comprising a dry powder reservoir to which a stream of propellant can be directed to disperse the powder or using a self-propelling solvent/powder-dispensing container such as a device comprising the particulate delivery system suspended in a low-boiling propellant in a sealed container. Dry powder compositions may include a solid fine powder diluent such as sugar and are conveniently provided in a unit dose form. Low boiling propellants generally include liquid propellants having a boiling point below 65 degrees F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the particulate delivery system).

Pharmaceutical compositions of the invention formulated for pulmonary delivery can also provide the active ingredient in the form of droplets of a suspension. Such formulations can be prepared, packaged, or sold as aqueous or dilute alcoholic suspensions, optionally sterile, comprising the particulate delivery system, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate.

The formulations described herein as being useful for pulmonary delivery are also useful for intranasal delivery of a pharmaceutical composition of the invention. Another formulation suitable for intranasal administration is a coarse powder comprising the particulate delivery system. Such a formulation is administered in the manner in which snuff is taken i.e. by rapid inhalation through the nasal passage from a container of the powder held close to the nares.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) particulate delivery system, the balance comprising an orally dissolvable or degradable composition and, optionally, one or more of the additional ingredients described herein. Alternately, formulations suitable for buccal administration can comprise a powder or an aerosolized or atomized solution or suspension comprising the particulate delivery system.

Antibodies

As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. Thus, these fragments are preferred, as well as the products of a Fab or other immunoglobulin expression library. Moreover, antibodies of the present invention include chimeric, single chain, and humanized antibodies.

Antibodies can be prepared using any number of techniques known in the art. Suitable techniques are discussed briefly below. The antibody may be polyclonal or monoclonal. Polyclonal antibodies can have significant advantages for initial development, including rapidity of production and specificity for multiple epitopes, ensuring strong immunofluorescent staining and antigen capture. Monoclonal antibodies are adaptable to large-scale production; preferred embodiments include at least one monoclonal antibody specific for an epitope of the target antigen. Because polyclonal preparations cannot be readily reproduced for large-scale production, another embodiment uses a cocktail of at least four monoclonal antibodies.

A single chain Fv ("scFv" or "sFv") polypeptide is a covalently linked $V_H$:$V_L$ heterodimer which may be expressed from a nucleic acid including $V_H$- and $V_L$-encoding sequences either joined directly or joined by a peptide-encoding linker. Huston, et al. Proc. Nat. Acad. Sci. USA, 85: 5879-5883 (1988). A number of structures for converting the naturally aggregated, but chemically separated, light and heavy polypeptide chains from an antibody V region into a scFv molecule which folds into a three dimensional structure substantially similar to the structure of an antigen-binding site. See, e.g. U.S. Pat. Nos. 6,512,097, 5,091,513 and 5,132,405 and 4,956,778.

In one class of embodiments, recombinant design methods can be used to develop suitable chemical structures (linkers) for converting two naturally associated, but chemically separate, heavy and light polypeptide chains from an antibody variable region into a sFv molecule which folds into a three-dimensional structure that is substantially similar to native antibody structure. Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which result in the minimum loss of residues from the polypeptide domains, and which necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and preferably are free of residues having large side groups which might interfere with proper folding of the $V_H$ and $V_L$ chains. Thus, suitable linkers under the invention generally comprise polypeptide chains of alternating sets of glycine and serine residues, and may include glutamic acid and lysine residues inserted to enhance solubility. Nucleotide sequences encoding such linker moieties can be readily provided using various oligonucleotide synthesis techniques known in the art.

Alternatively, a humanized antibody fragment may comprise the antigen binding site of a murine monoclonal antibody and a variable region fragment (lacking the antigen binding site) derived from a human antibody. Procedures for the production of chimeric and further engineered monoclonal antibodies include those described in Riechmann et al. (Nature 332: 323, 1988), Liu et al. (PNAS 84: 3439, 1987), Larrick et al. (Bio Technology 7: 934, 1989), and Winter and Harris (TIPS 14: 139, May, 1993).

One method for producing a human antibody comprises immunizing a nonhuman animal, such as a transgenic mouse, with a target antigen, whereby antibodies directed against the target antigen are generated in said animal. Procedures have been developed for generating human antibodies in non-human animals. The antibodies may be partially human, or preferably completely human. Non-human animals (such as transgenic mice) into which genetic material encoding one or more human immunoglobulin chains has been introduced may be employed. Such transgenic mice may be genetically altered in a variety of ways. The genetic manipulation may result in human immunoglobulin polypeptide chains replacing endogenous immunoglobulin chains in at least some (preferably virtually all) antibodies produced by the animal upon immunization. Antibodies produced by immunizing transgenic animals with a target antigen are provided herein.

Mice in which one or more endogenous immunoglobulin genes are inactivated by various means have been prepared. Human immunoglobulin genes have been introduced into the mice to replace the inactivated mouse genes. Antibodies produced in the animals incorporate human immunoglobulin polypeptide chains encoded by the human genetic material introduced into the animal. Examples of techniques for production and use of such transgenic animals are described in U.S. Pat. Nos. 5,814,318, 5,569,825, and 5,545,806, which are incorporated by reference herein.

Monoclonal antibodies may be produced by conventional procedures, e.g., by immortalizing spleen cells harvested from the transgenic animal after completion of the immunization schedule. The spleen cells may be fused with myeloma cells to produce hybridomas, by conventional procedures.

A method for producing a hybridoma cell line comprises immunizing such a transgenic animal with a immunogen comprising at least seven contiguous amino acid residues of a target antigen; harvesting spleen cells from the immunized animal; fusing the harvested spleen cells to a myeloma cell line, thereby generating hybridoma cells; identifying a hybridoma cell line that produces a monoclonal antibody that binds a target antigen. Such hybridoma cell lines, and monoclonal antibodies produced therefrom, are encompassed by the present invention. Monoclonal antibodies secreted by the hybridoma cell line are purified by conventional techniques.

In another embodiment, antibody fragments are produced by selection from a nonimmune phage display antibody repertoire against one set of antigens in the presence of a competing set of antigens (Stausbol-Grøn, B., et al., De novo identification of cell-type specific antibody-antigen pairs by phage display subtraction. Isolation of a human single chain antibody fragment against human keratin 14. Eur J Biochem 2001 May; 268(10):3099-107). This approach can be used to produce phage antibodies directed against target antigens. The protocol in general is based on that described by Stausbol-Grøn, B., et al., 2001, Briefly, a nonimmunized semisynthetic phage display antibody repertoire is used. The repertoire is a single chain Fv (scFv) phagemid repertoire constructed by recloning the heavy and light chain regions from the lox library (Griffiths, A. D., et al. (1994) Isolation of high affinity human antibodies directly from large synthetic repertoires. EMBO J. 13, 3245-3260). *Escherichia coli* TG1 (supE hsdD5 Δ(lac-proAB) thi F' {traD36 proAB+ lacI$^q$ lacZΔM15]) is an amber suppressor strain (supE) and is used for propagation of phage particles. *E. coli* HB2151 (ara A(lac-proAB) thi F {proAB+ lacI$^q$ lacZΔM15]) is a nonsuppressor strain and is used for expression of soluble scFv. In another embodiment, a human single-chain Fv (scFv) library can be amplified and rescued, as described (Gao, at al., Making chemistry selectable by linking it to infectivity, Proc. Natl. Acad. Sci. USA, Vol. 94, pp. 11777-11782, October 1997). The library is panned against target antigens suspended in PBS (10 mM phosphate, 150 mM NaCl, pH 7.4) and the positive scFv-phage are selected by enzyme-linked immunosorbent assay (EUSA).

In other preferred embodiments, an antibody is supplied by providing an expression vector encoding a recombinant antibody, preferably a single chain Fv antibody.

Example 1

FIG. 1 is a schematic diagram 100 of a transverse section of a yeast cell wall, showing, from outside to inside, an outer fibrillar layer 110, an outer mannoprotein layer 120, a beta glucan layer 130, a beta glucan layer-chitin layer 140, an inner mannoprotein layer 150, the plasma membrane 160 and the cytoplasm 170.

Preparation of WGP Particles

Whole Glucan Particles (WGP, Lot W0282) were previously obtained from Alpha-Beta Technology. In general, whole glucan particles are prepared from yeast cells by the extraction and purification of the alkali-insoluble glucan fraction from the yeast cell walls. The yeast cells are treated with an aqueous hydroxide solution without disrupting the yeast cell walls, which digests the protein and intracellular portion of the cell, leaving the glucan wall component devoid of significant protein contamination, and having substantially the unaltered cell wall structure of β(1-6) and β(1-3) linked glucans. Yeast cells (*S. cerevisae* strain R4) were grown to midlog phase in minimal media under fed batch fermentation conditions. Cells (~90 g dry cell weight/L) were harvested by batch centrifugation at 2000 rpm for 10 minutes. The cells were then washed once in distilled water and then resuspended in 1 liter of 1M NaOH and heated to 90 degrees Celsius. The cell suspension was stirred vigorously for 1 hour at this temperature. The insoluble material, containing the cell walls, was recovered by centrifuging at 2000 rpm for 10 minutes. This material was then suspended in 1 liter, 1M NaOH and heated again to 90 degrees Celsius. The suspension was stirred vigorously for 1 hour at this temperature. The suspension was then allowed to cool to room temperature and the extraction was continued for a further 16 hours. The insoluble residue was recovered by centrifugation at 2000 rpm for 10 minutes. This material was finally extracted in 1 liter, water brought to pH 4.5 with HCl, at 75 degrees Celsius for 1 hour. The insoluble residue was recovered by centrifugation and washed three times with 200 milliliters water, four times with 200 milliliters isopropanol and twice with 200 milliliters acetone. The resulting slurry was placed in glass trays and dried at 55 degrees Celsius under reduced pressure to produce 7.7 g of a fine white powder.

A more detailed description of whole glucan particles and a process of preparing them can be found in U.S. Pat. Nos. 4,810,646; 4,992,540; 5,028,703; 5,607,677 and 5,741,495, the teachings of which are incorporated herein by reference. For example, U.S. Pat. No. 5,028,703 discloses that yeast WGP particles can be produced from yeast cells in fermentation culture. The cells were harvested by batch centrifugation at 8000 rpm for 20 minutes in a Sorval RC2-B centrifuge. The cells were then washed twice in distilled water in order to prepare them for the extraction of the whole glucan. The first step involved resuspending the cell mass in 1 liter 4% w/v NaOH and heating to 100 degrees Celsius. The cell suspension was stirred vigorously for 1 hour at this temperature. The insoluble material containing the cell walls was recovered by centrifuging at 2000 rpm for 15 minutes. This material was then suspended in 2 liters, 3% w/v NaOH and heated to 75 degrees Celsius. The suspension was stirred vigorously for 3 hours at this temperature. The suspension was then allowed to cool to room temperature and the extraction was continued for a further 16 hours. The insoluble residue was recovered by centrifugation at 2000 rpm for 15 minutes. This material was finally extracted in 2 liters, 3% w/v NaOH brought to pH 4.5 with HCl, at 75 degrees Celsius for 1 hour. The insoluble residue was recovered by centrifugation and washed three times with 200 milliliters water, once with 200 milliliters dehydrated ethanol and twice with 200 milliliters dehydrated ethyl ether. The resulting slurry was placed on petri plates and dried.

Preparation of YGMP Particles

*S. cerevisiae* (100 g Fleishmans Bakers yeast) was suspended in 1 liter 1M NaOH and heated to 55 degrees Celsius. The cell suspension was mixed for 1 hour at this temperature. The insoluble material containing the cell walls was recovered by centrifuging at 2000 rpm for 10 minutes. This material was then suspended in 1 liter of water and brought to pH 4-5 with HCl, and incubated at 55 degrees Celsius for 1 hour. The insoluble residue was recovered by centrifugation and washed once with 1000 milliliters water, four times with 200 milliliters dehydrated isopropanol and twice with 200 milliliters acetone. The resulting slurry was placed in a glass tray and dried at room temperature to produce 12.4 g of a fine, slightly off-white, powder.

Preparation of YGMP Particles

*S. cerevisiae* (75 g SAF-Mannan) was suspended in 1 liter water and adjusted to pH 12-12.5 with 1M NaOH and heated to 55 degrees Celsius. The cell suspension was mixed for 1 hour at this temperature. The insoluble material containing the cell walls was recovered by centrifuging at 2000 rpm for 10 minutes. This material was then suspended in 1 liter of water and brought to pH 4-5 with HCl, and incubated at 55 degrees Celsius for 1 hour. The insoluble residue was recovered by centrifugation and washed once with 1000 milliliters water, four times with 200 milliliters dehydrated isopropanol and twice with 200 milliliters acetone. The resulting slurry was placed in a glass tray and dried at room temperature to produce 15.6 g of a fine slightly off-white powder.

Preparation of YCP Particles

Yeast cells (*Rhodotorula* sp.) derived from cultures obtained from the American Type Culture Collection (ATCC, Manassas, Va.) were aerobically grown to stationary phase in YPD at 30 degrees Celsius. *Rhodotorula* sp. cultures available from ATCC include Nos. 886, 917, 9336, 18101, 20254, 20837 and 28983. Cells (1 L) were harvested by batch centrifugation at 2000 rpm for 10 minutes. The cells were then washed once in distilled water and then resuspended in water brought to pH 4.5 with HCl, at 75 degrees Celsius for 1 hour. The insoluble material containing the cell walls was recovered by centrifuging at 2000 rpm for 10 minutes. This material was then suspended in 1 liter, 1M NaOH and heated to 90 degrees Celsius for 1 hour. The suspension was then allowed to cool to room temperature and the extraction was continued for a further 16 hours. The insoluble residue was recovered by centrifugation at 2000 rpm for 15 minutes and washed twice with 1000 milliliters water, four times with 200 milliliters isopropanol and twice with 200 milliliters acetone. The resulting slurry was placed in glass trays and dried at room temperature to produce 2.7 g of a fine light brown powder.

FIG. 2A is a diagram of the structure of a yeast cell wall particle; FIG. 2B is a fluorescence photomicrograph showing concanavalin-A-FITC (con-A-fluorescein isothiocyanate, Sigma Chemical, St. Louis, Mo.) staining of the mannan component of the yeast cell wall particles; FIG. 2C is a diagram of the structure of a YGMP beta glucan-mannan particle, FIG. 2D is a fluorescence photomicrograph showing punctuate con-A-FITC staining of a YGMP beta glucan-mannan particle; FIG. 2E is a diagram of the structure of a YGP beta glucan particle and FIG. 2F is a fluorescence micrograph showing the absence of con-A-FITC staining of a YGP beta glucan particle.

Concanavalin-A is a lectin that binds selectively to mannose. Concanavalin-A-FITC binding was evaluated by fluorescence microscopy in order to observe the amount and distribution pattern of mannan on the surface of various yeast cell wall preparations. Suspensions of Baker's yeast (Fleishmans Bakers yeast), YGMP and YGP in PBS+1 mM $MgCl_2$+1 mM $CaCl_2$ were prepared at a density of $1\times10^8$ particles/ml. Con-A-FITC stock was 1 mg/ml concanavalin-A-FITC in PBS+1 mM $MgCl_2$+1 mM $CaCl_2$. Labeling mixtures were prepared in microcentrifuge tubes consisting of:

100 μl PBS+1 mM $MgCl_2$+1 mM $CaCl_2$
2.5 μl yeast cell wall particle suspension
2.5 μl con-A-FITC stock solution.

The microcentrifuge tubes containing the labeling mixtures were incubated in the dark at room temperature for one hour. Yeast cell wall particles were collected by centrifugation (10,000 rpm for 10 minutes) followed by washing the pellet with 100 μl PBS three times. The washed yeast cell wall particles were resuspended in 100 μl PBS and transferred to a 96 well plate for examination with a fluorescence microscope. Photographs of exemplary fields are shown in FIGS. 2B, 2D and 2F.

Table 1 summarizes the results of analyses of the chemical composition of WGP particles, YGP particles, YGMP particles and YCP particles that were prepared as described above. Note that YGP particles and YGMP particles have lower beta-glucan higher protein compared to the prior art WGP particles. YGMP particles have a substantially higher mannan content compared to the other particle types. YCP particles have a substantially higher chitin+chitosan content compared to the other particle types.

TABLE 1

Chemical Composition of Yeast Cell Wall Materials

| Analyte | Method | WGP S. cerevisiae | YGMP S. cerevisiae | YGP S. cerevisiae | YCP Rhodotorula |
|---|---|---|---|---|---|
| Macromolecular Composition* | | | | | |
| Protein | Kjeldal | <1 | 4.5 | 4.9 | — |
| Fat | Base hydrolysis, Soxhlet extraction | <1 | 1.6 | 1.4 | — |
| Ash | Combustion | 1.2 | 1.9 | 1.6 | — |
| Carbohydrate Composition** | | | | | |
| Beta-Glucan | Enzymatic Hydrolysis | 90.3 | 41.9 | 77 | 6.5 |
| Chitin + chitosan (as glocosamine, n-acetyl glucosamine) | Monosac Analysis-Dionex | 2.1 | 2.3 | 2.4 | 68 |
| Mannan (as mannose) | Monosac Analysis-Dionex | <1 | 36.9 | 0.47 | 1.3 |
| Other Glucans (as non beta 1,3-glucose and other unmeasured sugars) | Monosac Analysis-Dionex | 6.2 | 10.9 | 11.2 | 0.2 |

*Results are reported % w/w of dry analyzed materials
**Results are reported % w/w carbohydrate
WGP—Whole Glucan Particle—Prior Art Technology
YGMP—Yeast Glucan-Mannan Particle
YGP—Yeast Glucan Particle
YCP—Yeast Chitin Particle Example 2

Hydrodynamic Volume of Yeast Cell Wall Particles

The hydrodynamic volume of yeast cell wall particles was determined as a measure of the payload capacity of the particles. A 1 g aliquot of yeast cell wall particles was weighed in a tared 15 ml centrifuge tube to determine the weight of the dry particles. Water (12.5 mil) was added to the tube, and the tube was vortexed to mix the suspension of yeast cell wall particles. The particles were allowed to swell and absorb water for 30 minutes. The particle suspension was centrifuged at 2000 rpm for 10 minutes. The water was removed, the tube was weighed, and the weight of water absorbed was calculated. The hydrodynamic volume was calculated as the ratio of the weight of the water absorbed to the weight of the dry particles. Table 2 presents the results for two preparations of the prior art WGP and the YGP and YGMP of the present invention.

TABLE 2

Hydrodynamic Volume of Exemplary Yeast Cell Wall Preparations

| Yeast Cell Wall Particle | Hydrodynamic Volume (g water/g particles) |
|---|---|
| WGP Prep 1 | 9.7 |
| WGP Prep 2 | 6.9 |
| YGP | 8.3 |
| YGMP | 6.7 |

The lower hydrodynamic volume of WGP Prep 2 may be due to an increased number of fragmented particles in this preparation. With respect to the other particles, the "purer" YGP had a higher hydrodynamic volume than the YGMP.

In general, the payload volume was limited to <66% hydrodynamic volume to ensure quantitative absorption of the payload by the yeast cell wall particles. By this rule, ≤5.5 µl payload would be loaded per mg YGP particles and ≤4.4 µl payload would be loaded per mg YGMP particles.

Example 3

Oral Bioavailability of YGP and YGMP

Fluorescently labeled yeast glucan particles (YGP-F) and fluorescently labeled yeast glucan-mannan particles (YGMP-F) were prepared for an uptake study. Starting materials were: 5 ml YGP (5 mg/ml in 0.1M borate buffer, pH 8), 5 ml YGMP (5 mg/ml in 0.1M borate buffer, pH8), dichlorotriazinyl aminofluorescein (DTAF), 20 mg/ml in DMSO, freshly prepared and 0.1M borate buffer, pH 8.

Labeling reactions were carried out at a 25 mg scale. Aliquots of 25 mg particles were suspended in 5 ml 0.1M borate buffer, pH 8 and sonicated to reduce clumps of particles to single particles. The particles were centrifuged and resuspended in 5 ml 0.1M borate buffer, pH 8. DTAF (0.5 ml 20 mg/ml) was added to the resuspended particles and incubated 2 days at 37 degrees Celsius. At the end of the incubation, 5 ml 1 M Tris buffer, pH 8.3, was added and the mixture was incubated 30 minutes to quench DTAF. The incubated particles were centrifuged and washed in PBS until the supernatants were no longer fluorescent. The washed particles were resuspended in PBS at 5 mg/ml. The number of particles in a 1:100 dilution of an aliquot was counted. Results: intensely fluorescent yeast cell wall particles were produced, at concentrations of $1.8 \times 10^9$ particles per ml YGP-F and $2.1 \times 10^9$ particles per ml YGMP-F.

The influence of the surface carbohydrate composition on the oral bioavailability of yeast glucan particles was studied to determine if the phagocytic particle uptake of a payload could be targeted via the mannose receptor as well as by the CR3/dectin-1 beta glucan receptors. The ability to target either or both receptors can expand the target population of cells beyond macrophages and dendritic cells.

The treatment groups are summarized in Table 3, below. Starting materials included: FITC-labeled yeast glucan particles (YGP-F), FITC-labeled yeast glucan-mannan particles (YGMP-F), a group of seven C57Black mice and a group of seven C57/B16 mice. Doses of YGP-F (1 mg/ml) and YGMP-F (3.7 mg/ml) were prepared to deliver equivalent number of particles in 0.1 ml PBS and administered by oral gavage to one mouse from each group daily for five days. The same dose was administered by subcutaneous injection of 0.1 ml to one mouse from each group daily for five days. On day four the cages were changed and fresh bedding was provided. Fecal pellets were collected on day 5 from each group into 15 ml conical tubes and frozen for processing later. The fecal pellets were processed by adding 5 ml water and holding at 4 degrees Celsius for 2 hours. The hydrated fecal pellets were homogenized using a Polytron homogenizer. Dilutions of homogenized feces were placed in a 96-well microtiter plate and microscopically examined under fluorescent and transmitted white light conditions for the presence of fluorescent particles. Aliquots having fluorescent particles were further diluted and the number of fluorescent particles/ml was counted with a hematocytometer.

Mice were sacrificed on day 7, and the spleen was removed from each animal and placed into separate tubes containing PBS on ice. The spleens were macerated with scissors and pressed through 70 micron screens to produce single cell suspensions. Aliquots of the single cell suspensions were retained and fixed in 1% formalin in PBS for quantifying the fraction of cells labeled with fluorescent particles using FACS. Cell suspensions are stained using a phycoerythrin (PE) labeled-antibody against macrophage marker, preferably murine Emr-1 (F4/80), which stains splenic red pulp macrophages, Kupffer cells, microglia and Langerhans cells.

Cell suspensions were plated at a density of $10^7$ cells per 60 mm petri dish in DMEM containing 10% fetal calf serum (JRH Scientific), penicillin-streptomycin and glutamine (Gibco) and incubated for 24 hours at 37 degrees Celsius under 5% $CO_2$ to allow for attachment. After the incubation, any unattached lymphocytes were washed away. The attached splenic macrophage cells were typsinized, fixed and scored for the fraction of adherent cells having fluorescent particles using a fluorescence microscope.

The administration of the fluorescent particles was well tolerated. Analysis of adherent splenic macrophages demonstrated the presence of fluorescent yeast cell wall particles in all fluorescent particle treated animals. These results demonstrate that both YGP-F and YGMP-F are orally bioavailable and can be systemically distributed by macrophages. The analysis of feces demonstrated the presence of fluorescent particles, indicating that oral absorption was incomplete at the dosage levels used. C57/B16 mice were able to absorb YGP-F and YGMP-F administered orally. The number of fluorescent particles in feces was quantified as an estimate of uptake efficiency.

TABLE 3

| Route | Treatment | Dose | mg/ml | # part./ml | # part./dose | Presence of Fluorescent Particles Splenic Macrophages | Feces |
|---|---|---|---|---|---|---|---|
| | Control | PBS control | — | — | — | | |
| SQ | YGP-F | 100 µg | 1 | $1 \times 10^9$ | $1 \times 10^8$ | + | − |
| Oral | YGP-F | 100 µg | 1 | $1 \times 10^9$ | $1 \times 10^8$ | + | + |

TABLE 3-continued

| Route | Treatment | Dose | mg/ml | # part./ml | # part./dose | Presence of Fluorescent Particles Splenic Macrophages | Feces |
|---|---|---|---|---|---|---|---|
| Oral | YGP-F | 33 µg | 0.33 | $3.3 \times 10^8$ | $3.3 \times 10^7$ | + | + |
| SQ | YGPM-F | 370 µg | 3.7 | $1 \times 10^9$ | $1 \times 10^8$ | + | − |
| Oral | YGPM-F | 370 µg | 3.7 | $1 \times 10^9$ | $1 \times 10^8$ | + | + |
| Oral | YGPM-F | 110 µg | 1.1 | $1 \times 10^8$ | $3.3 \times 10^7$ | + | + |
| Untreated Control | — | — | — | — | — | − | − |

Example 4

Preparation of Chitosan Loaded YGP Particles

YGP particles were prepared with a cationic trapping polymer, chitosan. 1% w/v chitosan solutions were prepared in 0.1M acetic acid using either High Molecular Weight (HMW) chitosan (~70,000 Mw, Sigma Chemical St. Louis, Mo.) or Low Molecular Weight (HMW) chitosan (~10,000 Mw, Sigma Chemical St. Louis, Mo.). Both 1% w/v HMW and LMW chitosan solutions were prepared in 0.1M acetic acid. Four ml HMW or LMW chitosan solution was added to 2 g YGP in a 50 ml conical centrifuge tube and mixed until a smooth paste was formed. The mixture was incubated for 1 hour at room temperature to allow the liquid to be absorbed. NaOH (40 ml, 0.1M) was added to each tube, which was vortexed immediately to precipitate the chitosan inside the YGP. The YGP:chitosan suspension was passed through an 18 gauge needle to produce a fine suspension of YGP:chitosan particles. The YGP:chitosan particles were collected by centrifugation (2,000 rpm for 10 minutes) followed by washing the pellet with deionized water until the pH of the supernatant was 7-8. The YGP:chitosan particles were then washed four times with two pellet volumes of isopropanol and then washed twice with two pellet volumes of acetone. The YGP:chitosan particles were then dried at room temperature in a hood. The procedure yielded 1.2 g YGP:LMW chitosan particles and 1.4 g YGP:HMW chitosan particles.

Example 5

Preparation of CytoPure™ Loaded YGP Particles

YGP particles were prepared with a biodegradable cationic trapping polymer, CytoPure™, a proprietary, commercially available, water-soluble cationic polymer transfection reagent (Qbiogene, Inc., CA). Twenty µl CytoPure™ was diluted in 0.5 ml deionized water and added to 0.5 g YGP in a 50 ml conical centrifuge tube and mixed until a smooth paste was formed. The mixture was incubated for 15 minutes at 4 degrees Celsius to allow the liquid to be absorbed. Twenty-five ml ethanol was added to each tube, which was vortexed immediately to precipitate the CytoPure™ inside the YGP. The YGP:CytoPure™ suspension was sonicated to produce a fine suspension of YGP:CytoPure™ particles. The YGP:CytoPure™ particles were collected by centrifugation (2,000 rpm for 10 minutes) followed by washing the pellet four times with two pellet volumes of isopropanol and then washed twice with two pellet volumes of acetone. The YGP:CytoPure™ particles were then dried at room temperature in a hood. The procedure yielded 0.45 g YGP:CytoPure™ particles.

Example 6

Preparation of Polyethylenimine Loaded YGP Particles

YGP particles were prepared with polyethylenimine (PEI) as a cationic trapping polymer. A 0.5 ml aliquot of a 2% w/v PEI (~50,000 Mw, Sigma Chemical Co., St. Louis, Mo.) solution in water was added to 0.5 g YGP in a 50 ml conical centrifuge tube and mixed until a smooth paste was formed. The mixture was incubated for one hour at room temperature to allow the liquid to be absorbed. Twenty-five ml ethanol was added to each tube, which was vortexed immediately to precipitate the PEI inside the YGP. The YGP:PEI suspension was passed through an 18 gauge needle to produce a fine suspension of YGP:PEI particles. The YGP:PEI particles were collected by centrifugation (2,000 rpm for 10 minutes) followed by washing the pellet four times with two pellet volumes of isopropanol and then washed twice with two pellet volumes of acetone. The YGP:PEI particles were then dried at room temperature in a hood. The procedure yielded 0.48 g YGP:PEI particles.

Example 7

Preparation of Alginate Loaded YGP Particles

YGP particles were prepared with alginate (F200 or F200L, Multi-Kem Corp., Ridgefield, N.J.) as an anionic trapping polymer. A 2 ml aliquot of a 1% w/v alginate solution in water was added to 1 g YGP in a 50 ml conical centrifuge tube and mixed to form a smooth paste. The mixture was incubated for one hour at room temperature to allow the liquid to be absorbed. The mixture was diluted with 40 ml of a 1% w/v calcium chloride aqueous solution. The YGP:alginate suspension was passed through an 18 gauge needle to produce a fine suspension of YGP:alginate particles. The YGP:alginate particles were collected by centrifugation (2,000 rpm for 10 minutes. The YGP:alginate particles were washed four times with two pellet volumes of isopropanol and then washed twice with two pellet volumes of acetone. The YGP:alginate particles were then dried at room temperature in a hood. The procedure yielded 0.95 g YGP:F200 alginate particles and 0.86 g YGP:F200L alginate particles.

Example 8

Preparation of Poly-L-lysine Loaded YGP and YGMP Particles

YGP and YGMP particles were prepared with Poly-L-lysine (PLL) as a trapping polymer. A 4 ml aliquot of a 1% w/v PLL (Sigma Chemical Co., St. Louis, Mo.) solution in water was added to 1 g YGP or YGMP in a 50 ml conical centrifuge tube. The mixture was incubated for 30 minutes at 55 degrees Celsius to allow the liquid to be absorbed. Ten ml ethanol was added to each tube, which was homogenized (Polytron homogenizer) to produce a fine suspension of YGP:PLL or YGMP:PLL particles. The YGP:PLL or YGMP:PLL particles were collected by centrifugation (2,000 rpm for 10 minutes. The YGP:PLL or YGMP:PLL were washed four times with two pellet volumes of isopropanol and then washed twice with two pellet volumes of acetone. The YGP:PLL or YGMP:PLL particles were then dried at room temperature in a hood. The procedure yielded 1.3 g YGP:PLL particles and 1.1 g YGMP:PLL particles. Microscopic evaluation showed no free PLL aggregates, only YGP:PLL or YGMP:PLL particles.

Example 9

Preparation of Xanthan Loaded YGP and YGMP Particles

YGP and YGMP particles were prepared with xanthan as an anionic trapping polymer. A 4 ml aliquot of a 1% w/v xanthan solution in water was heated to 55 degrees Celsius to reduce viscosity and added to 1 g YGP or YGMP in a 50 ml conical centrifuge tube. The mixture was incubated for 30 minutes at 55 degrees Celsius. Ten ml ethanol was added to each tube, which was homogenized (Polytron homogenizer) to produce a fine suspension of YGP:xanthan or YGMP:xanthan particles. The YGP:xanthan or YGMP:xanthan particles were collected by centrifugation (2,000 rpm for 10 minutes). The YGP:xanthan or YGMP:xanthan particles were washed four times with two pellet volumes of isopropanol and then washed twice with two pellet volumes of acetone. The YGP:xanthan or YGMP:xanthan particles were then dried at room temperature in a hood. The procedure yielded 1.2 g YGP:xanthan particles and 1.1 g YGMP:xanthan particles. Microscopic evaluation showed no free xanthan aggregates, only YGP:xanthan or YGMP:xanthan particles.

Example 10

Evaluation of Ability of YGP:Chitosan and YGP:Alginate to Bind Charged Dyes

YGP:Chitosan and YGP:Alginate particles were prepared as described in Examples 7 & 9 above. 0.1% w/v aqueous solutions of trypan blue (Benzamine blue; CI 23850), an anionic dye and xylene cyanol (acid blue, a cationic dye) were prepared. A 50 µl aliquot of a 0.1% w/v aqueous dye solution was added to 10 mg YGP, YGP:Chitosan or YGP:Alginate in microcentrifuge tubes and the mixture was incubated for 1 hour at room temperature. The pellets were washed with deionized water until the supernatant solutions were no longer colored. The color of the pellet was evaluated; the results are presented in Table 4, below.

TABLE 4

| | Pallet Color | |
|---|---|---|
| YGP Formulation | Trypan blue | Xylene cyanol |
| YGP | Tan | Tan |
| YGP:Chitosan | Blue | Tan |
| YGP:Alginate | Tan | Green |

Electrostatic interactions between insoluble trapping polymers inside YGP were capable of binding to oppositely charged low molecular weight model dye payloads.

Example 11

Use of YGP:Agarose to Trap Molecules by Physical Entrapment

YGP:Agarose was prepared to evaluate physical entrapment as a means to trap a payload in YGP. A 2% w/v solution of agarose (Sigma Chemical Co., St. Louis, Mo.) was prepared in TE, and cooled to 50 degrees Celsius. A 1 mg/ml stock solution of salmon sperm DNA in TE was diluted to 0.5 mg/ml DNA in TE or in 1% agarose at 50 degrees Celsius. A 500 mg aliquot of YGP was mixed with 500 al of DNA in TE or 500 µl of DNA in agarose at 50 degrees Celsius and the mixture was incubated 1 hour at 50 degrees Celsius. The mixture was then cooled for 1 hour in a refrigerator to solidify the agarose. After 1 hour, 10 mls of TE was added and the mixture was incubated overnight in refrigerator. The mixture was then centrifuged, and DNA in the supernatant was measured by absorption at 260 nm. About >80% of the applied DNA was retained by YGP:Agarose compared to <1% retained by the YGP:TE control. These results indicate that agarose effectively traps DNA inside YGP by physical entrapment.

Example 12

Use of YGP:Polyacrylamide to Trap Molecules by Physical Entrapment

YGP:Polyacrylamide was prepared to evaluate physical entrapment as a means to trap a payload in YGP. A 1 mg/mil stock solution of salmon sperm DNA in TE was diluted to 0.5 mg/ml DNA in TE or in 30% polyacrylamide/bis(Sigma Chemical Co., St. Louis, Mo.). TEMED (N,N,N',N'-Tetramethylethylenediamine) was added to each DNA mixture (1 µl TEMED to 5 mls of DNA solution), and a 2 ml aliquot of each solution was added to 1 g YGP. The result was mixed to form a uniform suspension and incubated 3 hours at room temperature. After the 3 hour incubation, 10 ml of TE was added and the mixture was incubated overnight in a refrigerator. The mixture was then centrifuged, and DNA in the supernatant was measured by absorption at 260 nm. About >95% of the applied DNA was retained by YGP:Polyacrylamide compared to <1% retained by the YGP:TE control. These results indicate that polyacrylamide is an effective trapping polymer to use to trap DNA inside YGP by physical entrapment.

Example 13

Loading YGP With A Small Molecule, Tetracycline

The antibiotic tetracycline (tet) was loaded into YGP using the relative insolubility of the tetracycline-calcium salt. Yeast cell wall particles used were YGP, YGP:F200 alginate and YGP: F200L alginate prepared as described above. Stock solutions were 1 M $CaCl_2$ and 100 mg/ml tetracycline HCl (Sigma Chemical Co., St. Louis, Mo.). The loading mixtures were set up as summarized in Table 5, below.

TABLE 5

| YGP (1 mg) | Tet (μl) | Water (μl) | 1M CaCl$_2$ (μl) | Loading A355* super | % tet bound | % tet w/w | Release A355 PBS | 0.1M HCl |
|---|---|---|---|---|---|---|---|---|
| — | — | — | 200 | 0 | — | — | — | — |
| — | 4 | 200 | — | 0.538 | — | — | — | — |
| — | 4 | — | 200 | 0.542 | — | — | — | — |
| YGP | — | — | 200 | 0.01 | — | — | — | — |
| YGP | 4 | 200 | — | 0.56 | 0 | — | — | — |
| YGP | 4 | — | 200 | 0.524 | <1 | — | — | — |
| YGP-F200 alginate | 4 | 200 | — | 0.405 | 24.8 | 9.9 | 3.6 | 4.9 |
| YGP-F200L alginate | 4 | 200 | — | 0.375 | 30.3 | 12.1 | 5.9 | 12.2 |

*1/100 dilution

The mixtures were incubated for 30 minutes at room temperature and then deionized water or 1 M CaCl$_2$ was added as indicated. After 60 minutes at room temperature, the mixtures were sonicated and were incubated for at least an additional 30 minutes at room temperature. The mixtures were then centrifuged (2,000 rpm for 10 minutes) and the presence of tetracycline was indicated by the yellow color of the pellet and that of the initial supernatant. The amount of tetracycline loading into the yeast cell wall particles was calculated from the loss of absorption at 355 nm, the peak of the tetracycline absorption spectrum. A dilution of 4 μl of the 100 mg/ml tetracycline HCl stock solution in 200 μl deionized water had an absorbance at 355 nm of 0.538 compared to a deionized water blank. Release of tetracycline from the loaded yeast cell wall particles into PBS or 0.1M HCl was also measured spectrophotometrically.

The results are summarized in Table 5, above. In general, while YGP:F200 alginate and YGP:F200L alginate pellets were yellow after washing, YGP pellets were not yellow, indicating little, if any, tetracycline loading either a the hydrochloride or the calcium salt in the absence of a trapping polymer. In contrast, tetracycline was effectively loaded and trapped in YGP:F200 alginate and YGP:F200L alginate formulations, with about 25-30% of the applied tetracycline load absorbed as the calcium alginate salt. Trapped tetracycline was released from YGP:F200 alginate and YGP:F200L alginate into 0.1M HCl. The trapped tetracycline was partially retained in YGP:F200 alginate and YGP:F200L alginate in PBS for 1 hour at 37 degrees Celsius, about 26.5-51.6% of 0.1M HCl extractable.

In summary, tetracycline was readily trapped as a calcium alginate salt complex in a YGP-alginate-calcium composition, but was not effectively loaded and retained within YGP alone. The tetracycline trapped as a calcium alginate complex in YGP:F200 alginate and YGP:F200L alginate was slowly released in PBS at 37 degrees Celsius and substantially released under acid conditions.

Example 14

Efficacy of Tet and YGP:Tet in Increasing In Vitro Microbiocidal Killing of J774 Macrophages YGP:alginate-tet was prepared as described in Example 13, above. The numbers of particles of YGP and YGP:alginate-tet per ml in the stock solutions were 9×10$^7$/ml and 6×10$^8$/ml, respectively.

TABLE 6

*S. aureus* Killing By J774 Murine Macrophages Loaded With YGP Particles

| YGP Tube | J774 5 × 10$^5$/ml | DMEM + C | YGP/tet 5 × 10$^7$/ml | μl | Particles/ml | S. aureus Killed | Fold Increased Killing |
|---|---|---|---|---|---|---|---|
| a | 1 ml | 0.1 ml | — | — | — | <1 × 10$^5$ | 1 |
| b | — | 1.1 ml | — | — | — | <1 × 10$^5$ | 1 |
| c | 1 ml | — | YGP | 100 | 3 × 10$^7$ | <1 × 10$^5$ | 1 |
| d | — | 1 ml | YGP | 100 | 3 × 10$^7$ | <1 × 10$^5$ | 1 |
| e | 1 ml | — | YGP:tet | 100 | 3.75 × 10$^6$ | 1 × 10$^8$ | 100 |
| f | — | 1 ml | YGP:tet | 100 | 3.75 × 10$^6$ | 1 × 10$^6$ | — |
| g | 1 ml | — | YGP:tet | 100 | 7.5 × 10$^6$ | >1 × 10$^8$ | >10 |
| h | — | 1 ml | YGP:tet | 100 | 7.5 × 10$^6$ | 1 × 10$^7$ | — |
| i | 1 ml | — | YGP:tet | 100 | 1.5 × 10$^7$ | >1 × 10$^8$ | — |
| j | — | 1 ml | YGP:tet | 100 | 1.5 × 10$^7$ | >1 × 10$^8$ | — |
| k | 1 ml | — | YGP:tet | 100 | 3 × 10$^7$ | >1 × 10$^8$ | — |
| l | — | 1 ml | YGP:tet | 100 | 3 × 10$^7$ | >1 × 10$^8$ | — |
| m | 1 ml | — | tet – 1.25 | 100 | 1.25 μg/ml | 1 × 10$^6$ | — |
| n | — | 1 ml | tet – 1.25 | 100 | 1.25 μg/ml | 1 × 10$^6$ | 1 |
| o | 1 ml | — | tet – 2.5 | 100 | 2.5 μg/ml | 1 × 10$^7$ | 3.3 |
| p | — | 1 ml | tet – 2.5 | 100 | 2.5 μg/ml | 3.3 × 10$^6$ | — |
| q | 1 ml | — | tet – 5 | 100 | 5 μg/ml | >1 × 10$^8$ | — |
| r | — | 1 ml | tet – 5 | 100 | 5 μg/ml | >1 × 10$^8$ | — |
| s | 1 ml | — | tet – 10 | 100 | 10 μg/ml | >1 × 10$^8$ | — |
| t | — | 1 ml | tet – 10 | 100 | 10 μg/ml | >1 × 10$^8$ | — |

One ml of murine macrophages, J774 ($5 \times 10^5$/ml) was combined with YGP, YGP:alginate-tet or tetracycline of various concentration as summarized in Table 6, above.

The J774 cells were cultured overnight in medium (DMEM containing 10% fetal calf serum without antibiotics or glutamine). The cultures were incubated with medium alone, tetracycline diluted in medium or particles diluted in medium for 1 hour with rotation at 37 degrees Celsius to permit phagocytosis of the particles. The microbial killing assay was set up in 96 well plates. The cultures were diluted in medium and incubated overnight to allow for metabolism and release of tet from phagocytosed YGP: alginate-tet particles. Bacterial challenge was added as indicated in Table 6 and the cultures were incubated 2 hours at 37 degrees Celsius in a $CO_2$ incubator to permit S. aureus phagocytosis and killing by the J774 murine macrophages. After this incubation, 200 µl LB Broth (Luria-Bertani Broth: 1.0% tryptone, 0.5% yeast extract, 1.0% NaCl) was added to each culture to lyze the macrophages. Cultures were incubated at 37 degrees Celsius in an incubator to permit outgrowth of surviving & aureus. Growth was monitored by change in pH as indicated by phenol red. The effects of YGP, YGP: alginate-tet or tetracycline were compared. The results are provided in the two right-most columns of Table 6.

About $7.5 \times 10^6$ YGP: alginate-tet particles produced an effect on macrophages roughly equivalent to about 2.5 µg/ml tetracycline HCl. The macrophages alone were relatively less effective than macrophages treated with tetracycline in either mode, and about as effective as macrophages treated with empty YGP alone. Macrophages in combination with free tetracycline in solution were not much more effective than tetracycline alone. Macrophages treated with YGP: alginate-tet particles showed significant synergy. In general, the results demonstrate that phagosome delivery of tetracycline into J774 macrophage cells enhances the killing capacity of J774 macrophage cells for S. aureus.

Example 15

Loading of Protein into YGP

The utility of the delivery system of the present invention for the retention, transport and delivery of therapeutic peptides or proteins, vaccine antigens or other peptides or proteins was evaluated using the mixed proteins of fetal calf serum. Yeast cell wall particles used were YGP, YGP-PEI and YGP-chitosan prepared as described above. Stock solutions were 45 ng/µl fetal calf serum (FCS) (Fetal Bovine Serum, JRH Biosciences, Lenexa, Kans.), 0.2% PE (Sigma Chemical Co., St. Louis, Mo.) in TE, 0.05 M phosphate buffer, pH 7.2 (P buffer) and 0.05 M phosphate buffer, pH 7.2, 1 M NaCl (P+salt buffer).

Four µl of FCS were added to 1 mg of YGP, YGP-P or YGP-CN in microcentrifuge tubes as indicated in Table 7 and the resulting mixture was incubated 60 minutes at room temperature to allow the liquid to be absorbed by the particles. After the incubation, 200 µl phosphate buffer or 200 µl PEI was as indicated in Table 7 and the resulting mixture was incubated 60 minutes at room temperature. After the incubation, 0.5 ml phosphate buffer was added, and after a further 5 minute incubation, the tubes were sonicated to produce single particles. The particles were pelleted by centrifuging at 10,000 rpm for 10 minutes and the supernatants were removed to fresh tubes. 0.5 ml 0.05M sodium phosphate buffer, pH 7.2+1M NaCl was added to the pellets, and after a further 5 minute incubation, the tubes were centrifuged at 10,000 rpm for 10 minutes and the high salt elution supernatants were removed to fresh tubes. The protein content of the supernatants was measured by absorbance at 280 nm.

TABLE 7

| Tube | YGP | 1° Load | 2° Load | P buffer (µl) | P + Salt buffer (µl) |
|---|---|---|---|---|---|
| 1 | — | 4 µl FCS | 200 µl P buffer | 500 | 500 |
| 2 | YGP | 4 µl FCS | 200 µl P buffer | 500 | 500 |
| 3 | YGP | 4 µl FCS | 200 µl 2% PEI | 500 | 500 |
| 4 | YGP-PEI | 4 µl FCS | 200 µl P buffer | 500 | 500 |
| 5 | YGP-CN | 4 µl FCS | 200 µl P buffer | 500 | 500 |

The protein loading results are shown in Table 8. YGP particles without a trapping molecule trapped only 5% of the presented protein. YGP particles that were loaded first with FCS protein and then exposed to PEI retained 47% of the protein load. YGP particles that were preloaded with a trapping polymer such as PEI or chitosan before exposure to the protein load such retained 68% and 60%, respectively, of the protein load.

TABLE 8

| Tube | YGP | Payload | Trapping Polymer | Unbound Protein (ng) | % Unbound Protein | Bound Protein (ng) | % Bound Protein |
|---|---|---|---|---|---|---|---|
| 1 | — | FCS | P buffer | 180 | 100 | — | — |
| 2 | YGP | FCS | P buffer | 180 | 95 | 10 | 5 |
| 3 | YGP | FCS | 2% PEI | 120 | 63 | 70 | 47 |
| 4 | YGP-PEI | FCS | P buffer | 60 | 32 | 130 | 68 |
| 5 | YGP-CN | FCS | P buffer | 80 | 40 | 120 | 60 |

The results demonstrate that serum proteins are not effectively loaded and trapped into YGP without trapping polymers. Using YGP that were preloaded with trapping polymers before exposure to the payload proteins resulted in increased protein trapping. Alternatively, proteins can be trapped inside YGP by first loading the protein, and then adding a soluble trapping polymer to sequester the protein within the particle.

Example 16

Comparison of Various Methods of Loading DNA into YGP

Several methods of loading salmon sperm DNA into YGP, YGP containing low molecular weight (LMW) chitosans or YGP containing high molecular weight (HMW) chitosans were evaluated.

a. Capillary Loading Followed by Ethanol Precipitation

Salmon sperm DNA Sigma, St. Louis, Mo.) was sheared by 40 passes through 18 gauge needle and diluted to a concentration of 0.1 mg/ml in 50 mM TE (Tris-HCl, pH 8, 2 mM EDTA). Loading volumes of the DNA solution were determined and mixed in centrifuge tubes in duplicate with 100 mg aliquots of YGP, YGP:LMW chitosan or YGP: HMW chitosan as in Example 2 and incubated 1 hour. The incubated mixtures were ethanol precipitated by adding 1.5 ml ethanol to each tube. The insoluble products were collected by centrifugation at 2,000 rpm for 10 minutes. 10 ml TE was added to each tube, incubated for 1 hr at 37 degrees Celsius, centrifuged 2,000 rpm for 10 minutes to sediment the insoluble YGP and the DNA content of the supernatant was determined by absorbance at 260 nm. The amount of DNA remaining in the YGP was calculated.

b. DNA Loading by Absorption

Loading volumes of the DNA solution were mixed in centrifuge tubes in duplicate with 100 mg aliquots of YGP, YGP:LMW chitosan or YGP:HMW chitosan as in Example 4a and incubated 1 hour. 10 ml TE was added to each tube, incubated for 1 hr at 37 degrees Celsius, centrifuged 2,000 rpm for 10 minutes to sediment the insoluble YGP. The DNA content of the supernatant was determined by absorbance at 260 nm. The amount of DNA remaining in the YGP was calculated.

c. DNA Loading by CTAB Trapping

Loading volumes of the DNA solution were mixed in centrifuge tubes in duplicate with 100 mg aliquots of YGP, YGP:LMW chitosan or YGP:HMW chitosan as in Example 4 and incubated 1 hour. The incubated mixtures were precipitated by adding 1.5 ml 2% hexadecyltrimethylammoniumbromide (also known as cetyltrimethylammonium bromide or CTAB) solution to each tube. 10 ml TE was added to each tube, which was incubated for 1 hr at 37 degrees Celsius, and centrifuged 2,000 rpm for 10 minutes to sediment the insoluble YGP. The DNA content of the supernatant was determined by absorbance at 260 nm. The amount of DNA remaining in the YGP was calculated.

The amount of DNA remaining in the YGP was calculated.

The results are presented in Table 9, below.

TABLE 9

| | % DNA bound in YGP | | |
|---|---|---|---|
| Method | YGP | YGP:LMW chitosan | YGP:HMW chitosan |
| Direct Loading | <1% | 32% | 70% |
| Direct Loading + Ethanol | <1% | Not done | Not done |
| Direct Loading CTAB trapping | >99% | >99% | 99% |
| Absorption Loading | <1% | 5% | 12% |

Simple DNA loading or precipitation failed to effectively load and trap DNA into the YGP. In contrast, the use of the cationic trapping polymer, chitosan, resulted in the formation of chitosan-DNA complexes that can trap DNA inside YGP. In addition, the cationic agent CTAB can be effectively used to trap loaded DNA into YGP.

Example 17

DNA Loading and Trapping

Fluorescent salmon sperm DNA was prepared by mixing 1 ml of a 1 mg/ml solution of salmon sperm DNA in 0.1M carbonate buffer pH 9.2 with 100 µl of a 1 mg/ml suspension of DTAF in 10 mM carbonate buffer ph 9.2. After overnight incubation at 37 degrees Celsius, 200 µl 1M Tris-HCl pH 8.3 was added and incubated for 15 minutes at room temperature. Then, 100 µl 1M NaCl and 3 mls ethanol were added to ethanol precipitate the DNA. After storage at −20 C overnight, the ethanol precipitate was collected by centrifugation at 10,000 rpm 15 minutes. The ethanol precipitate was washed with 70% ethanol until supernatant was clear and resuspended in 1 ml TE.

The YGP suspensions were incubated for 30 minutes at room temperature. After the incubation, 0.45 ml 95% ethanol was added to one set (YGP, YGP-P, YGP-Chitosan) of three tubes, 0.2 ml 2% PEI was added to two sets of three tubes and 0.2 ml 2% CTAB was added to another set of three tubes. After 30 minutes incubation at room temperature, 0.2 ml 2% CTAB was added to one set of the PEI tubes and incubation proceeded for a further 30 minutes. Ethanol (1 ml, 95%) was added and the YGPs were stored overnight at −20 degrees Celsius. The YGP suspensions were washed with 70% ethanol and resuspended in 0.5 ml PBS. Results were evaluated by fluorescence microscopy, and are shown in Table 10.

TABLE 10

| Particle | Treatment | YGP pellet | Fluorescence Microscopy Observation |
|---|---|---|---|
| YGP | ethanol | White | Not fluorescent |
| YGP-CN | ethanol | Yellow | Internal particle fluorescence |
| YGP-P | ethanol | Yellow | Internal particle fluorescence |
| YGP | 2% PEI | Yellow | Internal particle fluorescence |
| YGP-CN | 2% PEI | Yellow | Weak internal particle fluorescence |
| YGP-P | 2% PEI | Yellow | Weak internal particle fluorescence |
| YGP | 2% CTAB | Yellow | Internal particle fluorescence |
| YGP-CN | 2% CTAB | Yellow | Strong internal particle fluorescence |
| YGP-P | 2% CTAB | Yellow | Strong internal particle fluorescence |
| YGP | 2% PEI/2% CTAB | Yellow | Strong internal particle fluorescence |
| YGP-CN | 2% PEI/2% CTAB | Yellow | Internal particle fluorescence |
| YGP-P | 2% PEI/2% CTAB | Yellow | Internal particle fluorescence |

No significant trapping of fluorescent-labeled DNA occurred if only simple ethanol precipitation without a trapping polymer was used, demonstrating that the prior art technology is not effective as a DNA delivery system. Fluorescent-labeled DNA was clearly being trapped by cationic trapping polymers PEI or chitosan, or with the cationic detergent CTAP inside YGP particles. The best DNA trapping occurred when a combination of trapping polymer and CTAB was used, such as YGP:PEI:DNA: CTAB, YGP:chitosan:DNA:CTAB or YGP:DNA:PEI: CTAB.

Example 18

Fluorescently Labeled Plasmid DNA Loading and Trapping

YGP containing pIRES plasmid was prepared for transfection and expression of encoded EGFP in J774 cells, a murine macrophage derived cell line. Cationic trapping agents used included cationic polymers such as polyethylenimine (PEI), CytoPure™, a proprietary, commercially available, water-soluble cationic polymer transfection reagent (Qbiogene, Inc., CA), chitosan and a cationic detergent hexadecyltrimethyl-ammoniumbromide (CTAB). A preferred PEI is JetPEI, a commercially available linear polyethylenimine cationic polymer transfection reagent (Qbiogene, Inc., CA).

pIRES-EGFP (Clonetech, Calif.) contains the internal ribosome entry site (IRES) of the encephalomyocarditis virus (ECMV) between the MCS and the EGFP (enhanced green fluorescent protein) coding region. This permits both the gene of interest (cloned into the MCS) and the EGFP gene to be translated from a single bicistronic mRNA. pIRES-EGFP is designed for the efficient selection (by flow cytometry or other methods) of transiently transfected mammalian cells expressing EGFP and another protein of interest. To optimize the selection of cells expressing high levels of the protein of interest, pIRES-EGFP utilizes a partially disabled IRES sequence (1). This attenuated IRES leads to a reduced rate of translation initiation at the EGFP start codon relative to that of the cloned gene. This enables the selection of those cells in which the mRNA, and hence the target protein, is produced at high levels to compensate for a suboptimal rate of translation of EGFP. This vector can also be used to express EGFP alone or to obtain stably transfected cell lines without time-consuming drug and clonal selection. EGFP is a red-shifted variant of wild-type GFP that has been optimized for brighter fluorescence and higher expression in mammalian cells. (Excitation maximum=488 nm; emission maximum=509 nm) EGFP encodes the GFPmut1 variant, which contains the amino acid substitutions Phe-64 to Leu and Ser-65 to Thr. These mutations increase the brightness and solubility of GFP, primarily due to improved protein folding properties and efficiency of chromophore formation. EGFP also contains an open reading frame composed almost entirely of preferred human codons. This leads to more efficient translation and, hence, higher expression levels in eukaryotic cells, relative to wild type GFP.

Solutions prepared were: pIRES EGFP plasmid DNA, 0.72 µg/µl in water, 0.2% w/v PEI (Sigma) in TE, 2 µl CytoPure (Qbiogene)+48 µl 0.15M NaCl, 2 µl JetPEI (Qbiogene)+48 µl TE, 0.2% Spermidine in TE, 2% (aq) CTAB and phosphate buffered saline (PBS).

Fluorescent pIRES plasmid DNA was prepared by mixing 1 ml of a 1 mg/ml solution of pIRES DNA in 0.1M carbonate buffer pH 9.2 with 100 µl of a 1 mg/ml suspension of DTAF in 10 mM carbonate buffer pH 9.2. After overnight incubation at 37 degrees Celsius, 200 µl 1M Tris-HCl pH 8.3 was added and incubated for 15 minutes at room temperature. Then 100 µl 1M NaCl and 3 ml ethanol were added to ethanol precipitate the DNA. After storage at −20 degrees Celsius overnight, the ethanol precipitate was collected by centrifugation at 10,000 rpm 15 minutes. The ethanol precipitate was washed with 70% ethanol until supernatant was clear and resuspended in 1 ml TE.

The YGP suspensions were incubated for 30 minutes at room temperature. After the incubation, 0.45 ml 95% ethanol was added to one set (YGP, YGP-P, YGP-Chitosan) of three tubes, 0.2 ml 2% PEI was added to two sets of three tubes and 0.2 ml 2% CTAB was added to another set of three tubes. After 30 minutes incubation at room temperature, 0.2 ml 2% CTAB was added to one set of the PEI tubes and incubation proceeded for a further 30 minutes. Ethanol (1 ml, 95%) was added and the YGPs were stored overnight at −20 degrees Celsius. The YGP suspensions were washed with 70% ethanol and resuspended in 0.5 mil PBS.

J774 murine macrophages were plated in six well plates at a density of 2.5×10$^5$ cells per well and incubated overnight as described in Example 14. The transfections were performed as summarized in Table 11. The particles were added to the culture medium at a 10 particle per cell ratio and the plates were swirled to distribute particles. The cells were incubated for 4 hours. At end of the incubation period, the culture medium was removed, the cells were washed with PBS and fixed in 0.4% formalin in PBS.

TABLE 11

| Tube | pIRES µg/µl | vol µl | YGP mg | 0.2% PEI in TE | 0.2% Chitosan in Acetate buffer pH 5.5 | 2% CTAB | Ethanol |
|---|---|---|---|---|---|---|---|
| 1 | — | — | 1 | 200 µl | — | 200 µl | 800 µl |
| 2 | — | — | 1 | — | 200 µl | 200 µl | 800 µl |
| 3 | 1.8 | 4 | 1 | 200 µl | — | 200 µl | 800 µl |
| 4 | 1.8 | 4 | 1 | — | 200 µl | 200 µl | 800 µl |

Figure 3A:
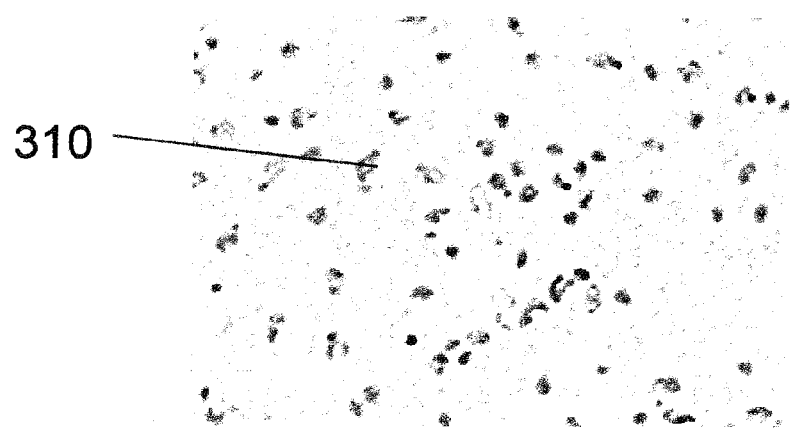
FIG. 3A is a reversed contrast (negative) grayscale image of a color light photomicrograph of cells exposed to YGP particles loaded with fluorescent labeled pIRES plasmid with PEI as the cationic trapping polymer and CTAB as a cationic detergent, indicating a cell 310
Figure 3B:
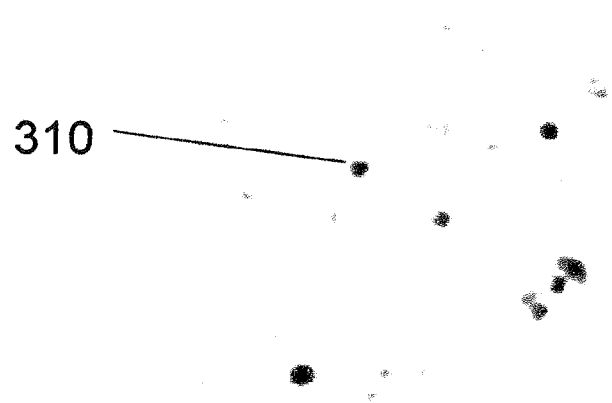
FIG. 3B is a reversed contrast (negative) grayscale image of a color fluorescence photomicrograph of the same field of cells showing bright staining representing fluorescent YGP particles internalized by the same cell 310 indicated in FIG. 3B.

Fluorescent DNA-containing particles and J774 cells incubated with fluorescent DNA-containing particles were evaluated by fluorescence microscopy, and results are summarized in Table 12 and shown in FIGS. 3A and 3B.

TABLE 12

| Particle Type | Treatment | Color of Pellet | Microscopic Examintation of Particles |
|---|---|---|---|
| YGP | ethanol | White | Not fluorescent |
| YGP-CN | ethanol | Yellow | Intracellular fluorescent particles |
| YGP-P | ethanol | Yellow | Intracellular fluorescent particles |
| YGP | 2% PEI | Yellow | Intracellular fluorescent particles |
| YGP-CN | 2% PEI | Yellow | Intracellular fluorescent particles |
| YGP-P | 2% PEI | Yellow | Intracellular fluorescent particles |
| YGP | 2% CTAB | Yellow | Intracellular fluorescent particles |
| YGP-CN | 2% CTAB | Yellow | Intracellular fluorescent particles |
| YGP-P | 2% CTAB | Yellow | Intracellular fluorescent particles |
| YGP | 2% PEI/2% CTAB | Yellow | FIGS. 3A & 3B; strongly fluorescent Intracellular particles |
| YGP-CN | 2% PEI/2% CTAB | Yellow | Intracellular fluorescent particles |
| YGP-P | 2% PEI/2% CTAB | Yellow | Intracellular fluorescent particles |

FIG. 3A is a reversed contrast (negative) grayscale image of a color light photomicrograph of cells exposed to YGP particles loaded with fluorescent labeled pIRES plasmid with PEI as the cationic trapping polymer and CTAB as a cationic detergent, indicating a cell 310. FIG. 3B is a reversed contrast (negative) grayscale image of a color fluorescence photomicrograph of the same field of cells showing bright staining representing fluorescent YGP particles containing fluorescent plasmid DNA internalized by the same cell 310 indicated in FIG. 3B.

Example 19

EGFP Expression by J774 Murine Macrophages Incubated with YGP:pIRES

The pIRES plasmid DNA was not fluorescently labeled in this Example, rather the functional expression of the green fluorescent protein (GFP) encoded by pIRES was used as a demonstration of uptake of loaded yeast cell wall particles, intracellular release of the pIRES DNA and expression of the GFP as evidenced by the production of fluorescence.

The YGP: pIRES formulations were prepared as summarized in Table 12, below. DNA was prepared from dilutions in deionized water of 1 mg/ml stock. The indicated amount of DNA solution was added to YGP and incubated for at least 30 minutes to allow for liquid absorption. The indicated amount of 0.2% PEI in TE or 0.2% chitosan in acetate buffer was added and the mixture was allowed to incubate for 5 minutes before sonication to produce single particles. After a further incubation of at least 30 minutes; the indicated amount of 2% CTAB was added. After an additional 5 minute incubation, the tubes were vortex mixed and incubated again for at least 30 minutes. The indicated amount of 95% ethanol was added. Each tube was then mixed and stored at −20 Celsius overnight. The YGP:pIRES formulated particles were then centrifuged, washed twice in 70% ethanol, collected by centrifugation at 10,000 rpm for 5 minutes, resuspended in 0.5 ml sterile PBS and sonicated to produce single particles. The number of particles per ml was counted and each formulation was and stored at −20 degrees Celsius.

J774 murine macrophages were plated in 6 well plates at a density of $2.5 \times 10^5$ cells per well and incubated overnight as described in Example 14. The transfections were performed as summarized in Table 11, above. The particles were added to the culture medium at a 10 particle per cell ratio and the plates were swirled to distribute particles. The cells were fed daily and incubated for 2 days. At end of the incubation period, the culture medium was removed the cells were washed with PBS and fixed in 0.4% formalin in PBS.

Figure 4A:
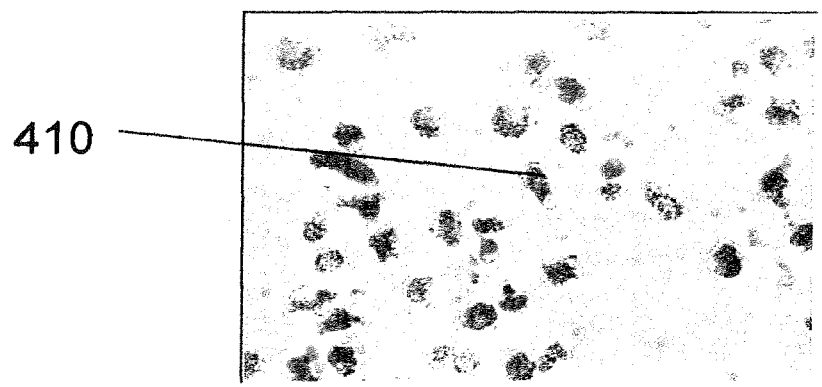
FIG. 4A is a reversed contrast (negative) grayscale image of a color fluorescence photomicrograph of cells, e.g., an indicated cell 410, exposed to fluorescent labeled YGP particles.
Figure 4B:
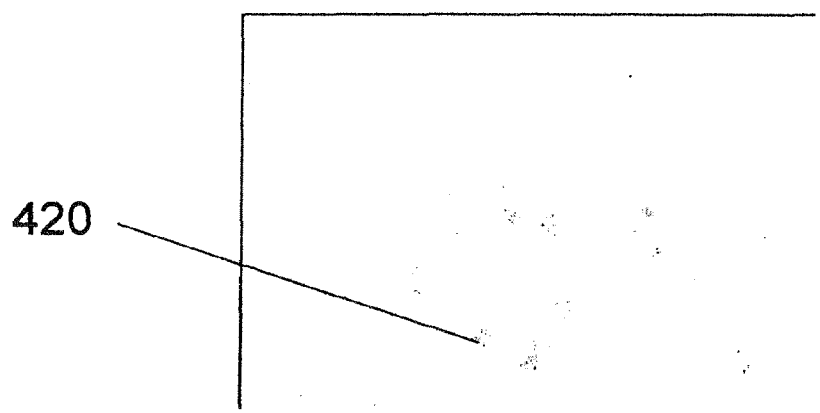
FIG. 4B is a reversed contrast (negative) grayscale image of a color fluorescence photomicrograph of cells, e.g., an indicated cell 420, exposed to YGP particles containing pIRES DNA, a cationic trapping polymer polyethylenimine (PEI) and cationic detergent hexadecyltrimethylammonium-bromide (also known as cetyltrimethylammonium bromide or CTAB) expressing GFP
Figure 4C:
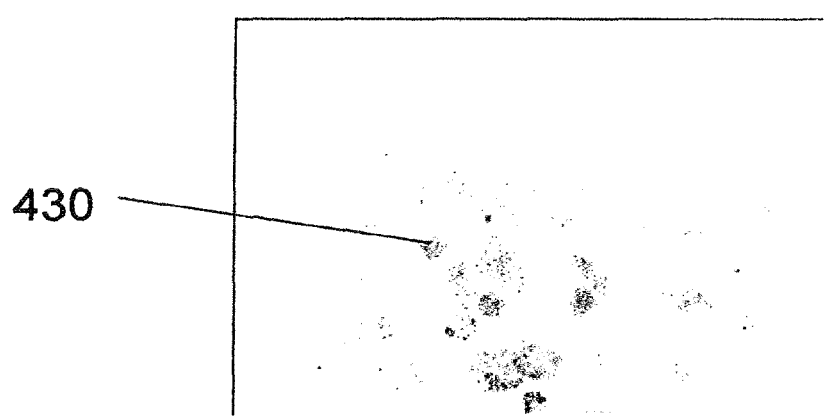
FIG. 4C is a reversed contrast (negative) grayscale image of a color fluorescence photomicrograph of cells, e.g., an indicated cell 430, exposed to YGP particles containing pIRES DNA, a cationic trapping polymer chitosan and cationic detergent CTAB expressing GFP.

The results are summarized in Table 13 and shown in FIGS. 4A-C. Cells were examined using fluorescence microscopy. Eighty nine percent of J774 cells took up YGP-F particles (Table 13, well 1B, FIG. 4A). EGFP expression was evident in >80% of J774 cells as punctate fluorescence in vacuoles in wells 1E (FIG. 4B) and 1F (FIG. 4C).

TABLE 13

| Well | Description | YGP/Cell | volume | Appearance |
|---|---|---|---|---|
| 1A | No Treatment Control | 0 | — | No detectible GFP fluorescent particles |
| 1B | YGPF Particle Uptake Control | 10 | 10 μl 1/10 | FIG. 4A, showing phagocytosis of fluorescent YGFP particles |
| 1C | YGP empty PEI/CTAB Control | 10 | 11 μl 1/10 | No detectible GFP fluorescent particles |
| 1D | YGP empty Chitosan/CTAB Control | 10 | 5 μl 1/10 | No detectible GFP fluorescent particles |
| 1E | YGP pIRES PEI/CTAB | 10 | 10 μl 1/10 | FIG. 4B, showing fluorescent GFP expression in cells |
| 1F | YGP pIRES Chitosan/CTAB | 10 | 6.5 μl 1/10 | FIG. 4C, showing fluorescent GFP expression in cells |

FIG. 4A is a reversed contrast (negative) grayscale image of a color fluorescence photomicrograph of cells, e.g., an indicated cell 410, exposed to fluorescent labeled YGP particles, FIG. 4B is a reversed contrast (negative) grayscale image of a color fluorescence photomicrograph of cells, e.g., an indicated cell 420, expressing GFP from pIRES DNA delivered by YGP with a cationic trapping polymer polyethylenimine (PEI) and cationic detergent hexadecyltrimethylammoniumbromide (also known as cetyltrimethylammonium bromide or CTAB) and FIG. 4C is a reversed contrast (negative) grayscale image of a color fluorescence photomicrograph of cells, e.g., an indicated cell 430, expressing GFP from pIRES DNA delivered by YGP with a cationic trapping polymer chitosan and cationic detergent CTAB.

Example 20

Fluorescent DNA, Oligonucleotide and siRNA Oligonucleotide Delivery into J774 Cells Using YGP-Cation Trapping Polymer Technology The following materials were used: YGP:Fluorescent salmon sperm DNA:PEI:CTAB particles, YGP:Fluorescent oligonucleotide:PEI:CTAB particles, and YGP:Fluorescent siRNA:PEI:CTAB. The fluorescent oligonucleotide was an 18 mer synthesized by Sigma Genosys with a fluorescein residue attached to the 5' end:

SEQ ID NO: 1
5' Fluorescein-TTGGTCATCCATGGCTCT 3'.

The fluorescent siRNA was a 21 mer non-silencing control siRNA synthesized with a fluorescein residue attached to the 5' end (Qiagen, Valencia, Calif., Catalog No. 1022079):

SEQ ID NO: 2
5' Fluorescein-UUCUCCGAACGUGUCACGUdTdT 3'.

J774 murine macrophages were plated in 6 well plates at a density of $2.5 \times 10^5$ cells per well and incubated overnight as described in Example 14. The transfections were performed as summarized in Table 14. The control and polynucleotide-loaded particles were added to the culture medium and the plates were swirled to distribute particles. The cells were fed daily and incubated for 24 hours. At end of the incubation period, the culture medium was removed the cells were washed with PBS and fixed in 0.4% formalin in PBS.

TABLE 14

| Well | Cells | YGP/Cell Ratio | Particles |
|---|---|---|---|
| 1A | J774 | 0 | — |
| 1B | J774 | 10 | YGPF |
| 1C | J774 | 10 | YGP DNAF |
| 1D | J774 | 10 | YGP oligoF |
| 1E | J774 | 10 | YGP RNAiF |

The results are illustrated in FIGS. 5A-I. Cells were examined using fluorescence microscopy and FACS. 92% of J774 cells took up YGP-F particles (Table 14, well IB, FIG. 5A). Fluorescent oligonucleotide (SEQ ID NO:1) delivery was evident in >80/a of J774 cells as punctate endosomal fluorescence and diffuse cytoplasmic fluorescence. Fluorescent non-silencing siRNA (SEQ ID NO:1) delivery was evident in >80% of J774 cells as punctate endosomal fluorescence and diffuse cytoplasmic fluorescence.

Figure 5A:
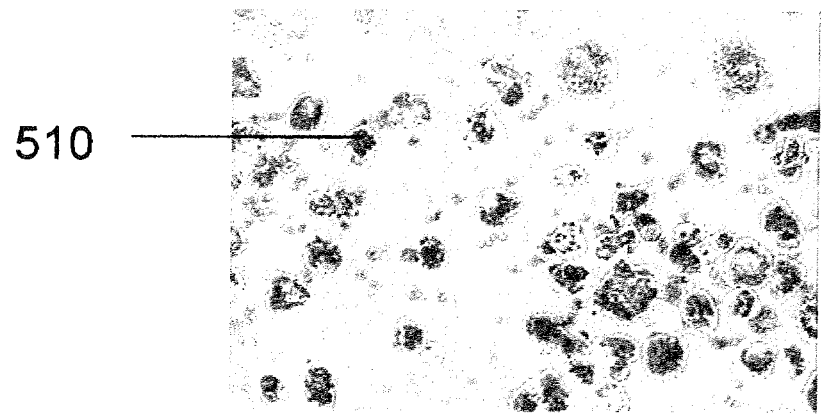
FIG. 5A is a reversed contrast (negative) grayscale image of a color combined light and fluorescence photomicrograph of cells, e.g., an indicated cell 510, exposed to fluorescent labeled YGP particles.
Figure 5B:
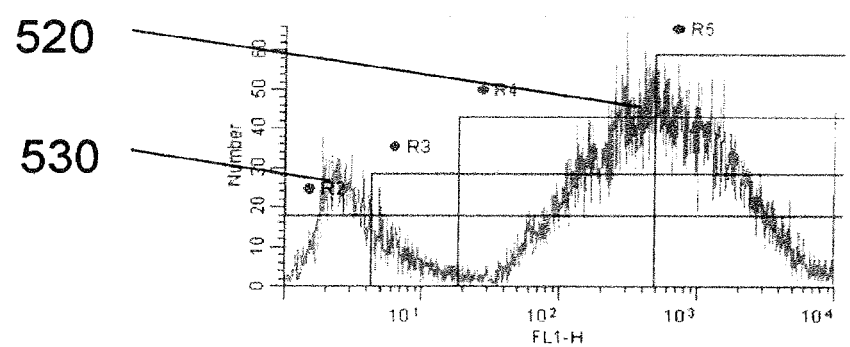
FIG. 5B is a graphic representation of the results of a fluorescence activated cell sorting (FACS) study showing a major peak 520 representing the distribution of signals from cells that have internalized fluorescent labeled YGP particles and a minor peak 530 representing the distribution of signals from cells without fluorescent labeled YGP particles.
Figure 5C:
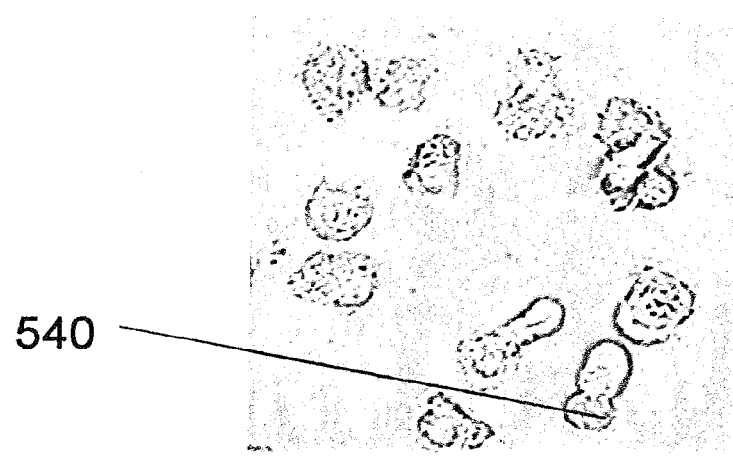
FIG. 5C is a reversed contrast (negative) grayscale image of a color light photomicrograph of cells, e.g., an indicated cell 540, exposed to YGP particles containing fluorescent labeled DNA, a cationic trapping polymer PEI and cationic detergent CTAB.
Figure 5D:
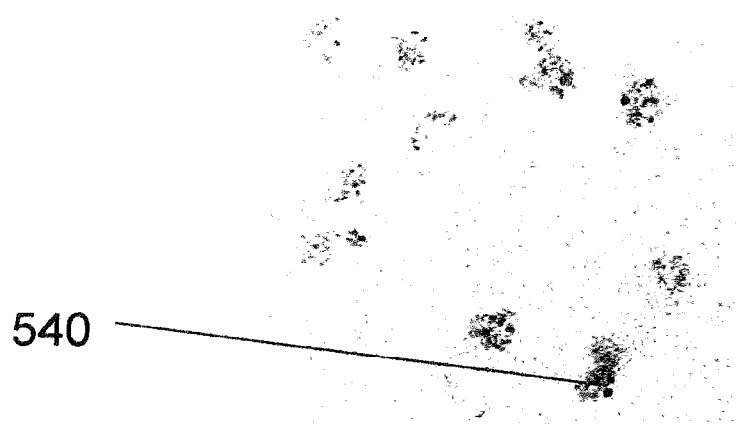
FIG. 5D is a reversed contrast (negative) grayscale image of a color fluorescence photomicrograph of the same field of cells showing the same indicated cell 540.
Figure 5E:
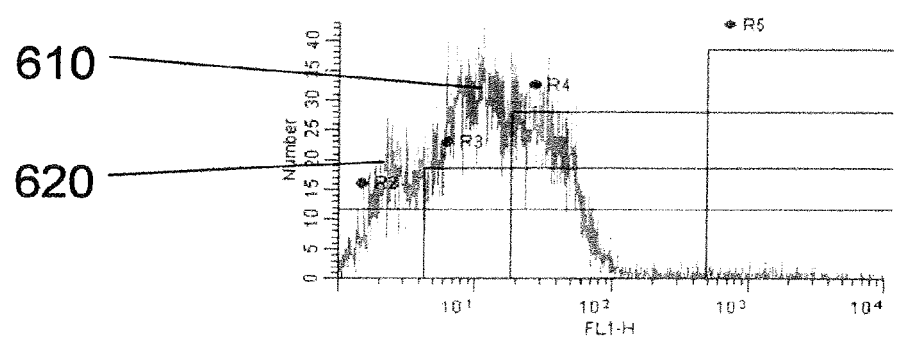
FIG. 5E is a graphic representation of the results of a FACS study showing a major peak 610 representing the distribution of signals from cells that have internalized YGP particles with fluorescent DNA payload and a shoulder 620 representing the distribution of signals from cells without YGP particles.
Figure 5F:
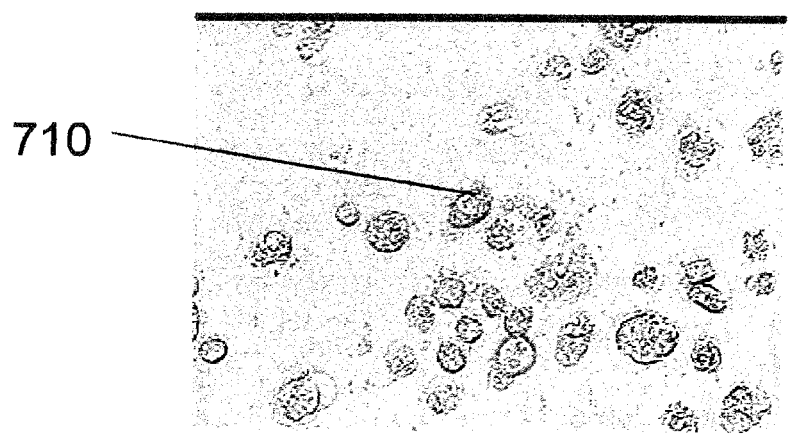
FIG. 5F is a reversed contrast (negative) grayscale image of a color light photomicrograph of cells, e.g., an indicated cell 710, incubated with YGP particles containing fluorescent antisense RNA payload.
Figure 5G:
FIG. 5G is a reversed contrast (negative) grayscale image of a color fluorescence photomicrograph of the same field of cells showing the same indicated cell 710.
Figure 5H:
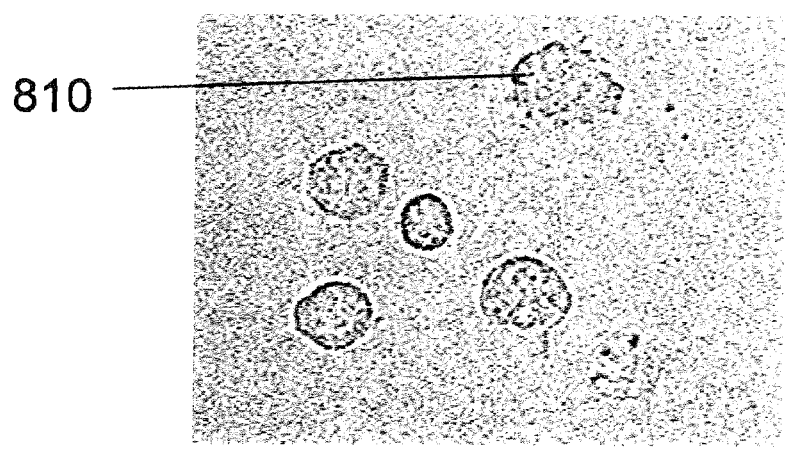
FIG. 5H is a reversed contrast (negative) grayscale image of a color light micrograph of cells, e.g., an indicated cell 810, incubated with YGP particles containing fluorescent labeled siRNA, PEI and CTAB
Figure 5I:
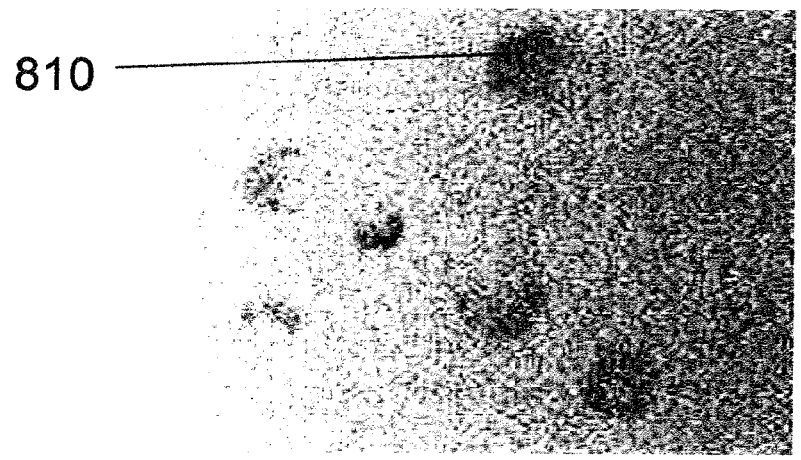
FIG. 5I is a reversed contrast (negative) grayscale image of a color fluorescence photomicrograph of the same field of cells showing the same indicated cell 810 containing internalized YGP particles with fluorescent RNAi payload.

FIG. 5A is a reversed contrast (negative) grayscale image of a color combined light and fluorescence photomicrograph of cells, e.g., an indicated cell 510, exposed to fluorescent labeled YGP particles; FIG. 5B is a graphic representation of the results of a fluorescence activated cell sorting (FACS) study showing a major peak 520 representing the distribution of signals from cells that have internalized fluorescent labeled YGP particles and a minor peak 530 representing the distribution of signals from cells without fluorescent labeled YGP particles; FIG. 5C is a reversed contrast (negative) grayscale image of a color light photomicrograph of cells, e.g., an indicated cell 540, exposed to YGP particles containing fluorescent labeled DNA, a cationic trapping polymer PEI and cationic detergent CTAB; FIG. 5D is a reversed contrast (negative) grayscale image of a color fluorescence photomicrograph of the same field of cells showing the same indicated cell 540, FIG. 5E is a graphic representation of the results of a FACS study showing a major peak 610 representing the distribution of signals from cells that have internalized YGP particles with fluorescent DNA payload and a shoulder 620 representing the distribution of signals from cells without YGP particles; FIG. 5F is a reversed contrast (negative) grayscale image of a color light photomicrograph of cells, e.g., an indicated cell 710, incubated with YGP particles containing fluorescent labeled antisense RNA, PEI and CTAB; FIG. 5G is a reversed contrast (negative) grayscale image of a color fluorescence photomicrograph of the same field of cells showing the same indicated cell 710 containing internalized YGP particles with fluorescent antisense RNA payload; FIG. 5H is a reversed contrast (negative) grayscale image of a color light micrograph of cells, e.g., an indicated cell 810, incubated with YGP particles containing fluorescent labeled siRNA, PEI and CTAB and FIG. 5I is a reversed contrast (negative) grayscale image of a color fluorescence photomicrograph of the same field of cells showing the same indicated cell 810 containing internalized YGP particles with fluorescent RNAi payload.

In summary, fluorescent DNA, oligonucleotide or siRNA payloads loaded into YGP using a cationic trapping polymer efficiently delivers the payload into J774 cells. Payloads are released from the endosomal compartment within 24 hours into the cytoplasm and nuclear compartments.

The claims should not be read as limited to the described order or elements unless stated to that effect. Therefore, all embodiments that come within the scope and spirit of the following claims and equivalents thereto are claimed as the invention.

What is claimed:

1. A particulate delivery system comprising an extracted yeast cell wall comprising less than 90 weight percent beta-glucan, a payload molecule and a payload trapping molecule, wherein the payload trapping molecule is contained within an interior space defined by the extracted yeast cell wall, wherein the payload trapping molecule is present in an amount sufficient to facilitate retention of the payload molecule within the extracted yeast cell wall, and wherein the payload molecule is selected from the group consisting of a polynucleotide and a small organic active agent.

2. The particulate delivery system of claim 1 wherein the payload trapping molecule is:
   (a) a polysaccharide selected from the group consisting of agarose, an alginate, a xanthan, a dextran, a chitosan, a galactomannan gum, a derivative thereof and a mixture thereof;
   (b) a polyacrylamide;
   (c) a polyamide;
   (d) selected from the group consisting of a cationic polymer, an anionic polymer, a cationic detergent, an anionic detergent and a mixture thereof;
   (e) a cationic polymer selected from the group consisting of chitosan, polyethylenimine poly-L-lysine, a protein, a polypeptide, a short synthetic peptide, a helical amphiphilic peptide, a cationic dendrimers, glucaramide polymer, a N-substituted glycine oligomer, poly (2-methyl-acrylic acid 2-[(2-dimethylamino)-ethyl)-methyl-amino]-ethyl ester), poly(2-dimethylamino ethyl)-methacrylate and mixtures thereof;

(f) hexadecyltrimethylammoniumbromide;

(g) selected from the group consisting of a cationic polyelectrolyte, an anionic polyelectrolyte and an amphoteric polyelectrolyte;

(h) a cationic polyelectrolyte selected from the group consisting of a copolymer of vinyl pyrollidone and quaternary methyl methacrylate, a substituted polyacrylamide, polyethyleneimine, polypropyleneimine, a polyamine homopolymer, a polyamine co-polymer, polydiallyl dimethyl ammonium chloride, substituted dextrans; modified guar gum, a substituted protein, a polyamino acid, spermine and spermidine; or (i) an anionic polyelectrolyte selected from the group consisting of a copolymer of methyl vinyl ether and maleic anhydride, a copolymer of methyl vinyl ether and maleic acid, alginic acid a carboxymethyl cellulose, a substituted polyacrylamide, a polyacrylic acid, a polystyrene sulfonic acid, a dextran sulphates, a substituted saccharide, heparin and pharmaceutically acceptable salts.

3. The particulate delivery system of claim 1 wherein the payload molecule is a polynucleotide selected from the group consisting of an oligonucleotide, an antisense construct, a siRNA, an enzymatic RNA, a recombinant DNA construct and a mixture thereof.

4. The particulate delivery system of claim 3 wherein the recombinant DNA construct is an expression vector comprising a control element operatively linked to an open reading frame encoding a protein.

5. The particulate delivery system of claim 4 wherein the protein encoded by the open reading frame is a structural protein, a protein having enzymatic activity, a membrane protein, a DNA binding protein or a signaling protein.

6. The particulate delivery system of claim 1 wherein the payload molecule is a polynucleotide that comprises a nucleotide sequence that restores the function of an absent, defective or inhibited gene.

7. The particulate delivery system of claim 4 wherein the protein encoded by the open reading frame is selected from the group consisting of growth hormone, prolactin, placental lactogen, erythropoietin, thrombopoietin, interleukin-2, interleukin-3, interleukin-4, interleukin-5, interleukin-6, interleukin-7, interleukin-9, interleukin-10, interleukin-11, interleukin-12 (p35 subunit), interleukin-13, interleukin-15, oncostatin M, ciliary neurotrophic factor, leukemia inhibitory factor, alpha interferon, beta interferon, gamma interferon, omega interferon, tau interferon, granulocyte-colony stimulating factor, granulocyte-macrophage colony stimulating factor, macrophage colony stimulating factor, cardiotrophin-1 growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; factor VIIIC, factor IX tissue factor, von Willebrands factor, Protein C, atrial natriuretic factor, lung surfactant, urokinase, tissue-type plasminogen activator, bombazine, thrombin, alpha tumor necrosis factor, beta tumor necrosis factor, enkephalinase; RANTES, human macrophage inflammatory protein, serum albumin, mullerian-inhibiting substance, relaxin A-chain, relaxin B-chain, prorelaxin, mouse gonadotropin-associated peptide, DNase, inhibin, activin, vascular endothelial growth factor, a hormone receptor, a growth factors receptor, an integrin, protein A, protein D, a rheumatoid factor, a neurotrophic factor, bone-derived neurotrophic factor (BDNF), neurotrophin-3, neurotrophin-4, neurotrophin-5, or neurotrophin-6, NGF-beta, platelet-derived growth factor (PDGF); alpha fibroblast growth factor, beta alpha fibroblast growth factor, epidermal growth factor, transforming growth factor-alpha, transforming growth factor-beta1, transforming growth factor-beta2, transforming growth factor-beta3, transforming growth factor-beta4, transforming growth factor-beta5, insulin-like growth factor-I, insulin-like growth factor-II, des(1-3)-insulin-like growth factor-I, a insulin-like growth factor binding protein, CD3, CD4, CD8, CD19, CD20, an osteoinductive factor, an immunotoxin, a bone morphogenetic protein, a T-cell receptor, surface membrane proteins, decay accelerating factor, a viral antigen, a transport protein, homing receptor, an addressin, a regulatory protein, an immunoadhesin, an antibody and biologically active fragments or variants thereof.

8. The particulate delivery system of claim 1 wherein the small organic active agent is:

(a) an oligomer of heterocyclic polyamides that binds to the minor groove of double stranded DNA in a sequence specific manner;

(b) an oligomer having monomeric subunits selected from the group consisting of N-methylimidazole carboxamide, N-methylpyrrole carboxamide, beta-alanine and dimethylaminopropylamide;

(c) a contraceptive agent, a gastrointestinal therapeutic agent, a non-steroidal antifertility agent, a parasympathomimetic agent, a psychotherapeutic agent, a major tranquilizer, a minor tranquilizer, a rhinological decongestant, a sedative-hypnotic, a steroid, a sulfonamide, a vaccine; a vitamin, a nutrient, an antimalarial, an anti-migraine agent, an anti-Parkinson agent, an anti-spasmodic, an anticholinergic agent, an antitussive, a bronchodilator, a cardiovascular agent; an anti-hypertensive agent, a coronary vasodilator, an organic nitrate, an alkaloid, an analgesic, a narcotic, an anti-cancer agent, an anti-convulsant, an anti-emetic, an anti-inflammatory agent, a cytotoxic drug or an antibiotic; or (d) an antibiotic selected from the group consisting of a cephalosporin, chloramphenical, gentamicin, kanamycin A, kanamycin B, a penicillin, ampicillin, streptomycin A, antimycin A, chloropamtheniol, metronidazole, oxytetracycline, penicillin G, a tetracycline and mixtures thereof.

9. An article of manufacture comprising a first container containing a payload molecule selected from the group consisting of a nucleic acid composition, protein composition, small organic molecule and mixtures thereof, a second container containing the particulate delivery system of claim 1 and instructions for use.

10. A pharmaceutical composition comprising the particulate delivery system of claim 1, comprising a payload molecule selected from the group consisting of a polynucleotide, a protein, a small organic molecule and a mixture thereof, and a pharmaceutically acceptable excipient.

11. A method of delivering a payload molecule to a cell comprising the steps of:

providing an extracted yeast cell wall comprising beta-glucan, the yeast cell wall defining an internal space;

contacting the extracted yeast cell wall with a payload molecule wherein the payload molecule becomes at least partially enclosed within the internal space;

contacting the extracted yeast cell wall with a payload trapping molecule wherein the payload trapping molecule at least partially confines the payload molecule within the extracted yeast cell wall to form a particulate delivery system, wherein the payload molecule and the payload trapping molecule are soluble in the same solvent system; and contacting the cell with the particulate delivery system of claim 1; and incubating the cell for a time sufficient to facilitate internationalization of the particulate delivery system by the cell.

12. A method of making a particulate delivery system according to claim 1 comprising the steps of:

providing an extracted yeast cell wall comprising less than 90 weight percent beta-glucan, the yeast cell wall defining an internal space;

contacting the extracted yeast cell wall with a payload molecule wherein the payload molecule becomes associated with extracted yeast cell wall; and contacting the extracted yeast cell wall with a payload trapping molecule wherein the payload trapping molecule stabilizes the association of the payload molecule and the extracted yeast cell wall to form a particulate delivery system, wherein the payload trapping molecule is present in an amount sufficient to facilitate retention of the payload molecule within the yeast cell wall.

13. A method of exposing an individual to an antigen comprising the step of contacting a phagocytic cell of the individual with the particulate delivery system of claim 1 comprising a payload molecule, wherein the payload molecule is an antigenic molecule.

14. A method of immunizing an individual against a hyperproliferative disease comprising the step of contacting cells of said individual with the particulate delivery system of claim 1 comprising a payload molecule that is a polynucleotide comprising a control element operatively linked to an open reading frame encoding a peptide that comprises an epitope identical to, or substantially similar to, an epitope displayed on a hyperproliferative disease-associated protein, wherein encoded peptide is capable of being expressed in the cells of the individual.

15. A method of treating an individual suffering from a genetic disease comprising the step of contacting cells of said individual with the particulate delivery system of claim 1 comprising a payload molecule that is a polynucleotide comprising a nucleotide sequence that restores the activity of an absent, defective or inhibited gene.

\* \* \* \* \*